(12) United States Patent
Hastings et al.

(10) Patent No.: US 8,298,149 B2
(45) Date of Patent: Oct. 30, 2012

(54) SYSTEMS AND METHODS FOR MAKING AND USING A MOTOR DISTALLY-POSITIONED WITHIN A CATHETER OF AN INTRAVASCULAR ULTRASOUND IMAGING SYSTEM

(75) Inventors: Roger N. Hastings, Maple Grove, MN (US); Michael J. Pikus, Golden Valley, MN (US); Tat-Jin Teo, Sunnyvale, CA (US); Kevin D. Edmunds, Ham Lake, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 333 days.

(21) Appl. No.: 12/415,724

(22) Filed: Mar. 31, 2009

(65) Prior Publication Data

US 2010/0249603 A1 Sep. 30, 2010

(51) Int. Cl.
*A61B 8/14* (2006.01)
(52) U.S. Cl. .......................... 600/467; 600/459; 600/462
(58) Field of Classification Search .................. 600/407, 600/433, 435, 437, 444, 445, 459, 462, 467
See application file for complete search history.

(56) References Cited

U.S. PATENT DOCUMENTS

| | | | |
|---|---|---|---|
| 4,674,515 A | 6/1987 | Andou et al. | |
| 4,732,156 A | 3/1988 | Nakamura | |
| 4,975,607 A * | 12/1990 | Hara et al. | 310/67 R |
| 5,000,185 A * | 3/1991 | Yock | 600/459 |
| 5,095,911 A | 3/1992 | Pomeranz | |
| 5,176,141 A | 1/1993 | Bom et al. | |
| 5,240,003 A | 8/1993 | Lancee et al. | |
| 5,271,402 A | 12/1993 | Yeung et al. | |
| 5,313,950 A * | 5/1994 | Ishikawa et al. | 600/462 |
| 5,353,798 A | 10/1994 | Sieben | |
| 5,361,768 A * | 11/1994 | Webler et al. | 600/445 |
| 5,373,849 A | 12/1994 | Maroney et al. | |
| 5,375,602 A * | 12/1994 | Lancee et al. | 600/463 |
| 5,400,788 A | 3/1995 | Dias et al. | |
| 5,427,107 A | 6/1995 | Milo et al. | |

(Continued)

FOREIGN PATENT DOCUMENTS

DE 3714747 11/1988

(Continued)

OTHER PUBLICATIONS

Lancee, C.T. et al.; Future Directions in Intravascular Ultrasound: From Micro-Motors to Imaging Guidewire Systems; Echocardiography: A Jrnl. of CV Ultrasound & Allied Tech.; vol. 12, No. 3, 1995; pp. 275-281.

(Continued)

*Primary Examiner* — James Kish
*Assistant Examiner* — Michael N Fisher
(74) *Attorney, Agent, or Firm* — Vidas, Arrett & Steinkraus

(57) ABSTRACT

A catheter assembly for an intravascular ultrasound system includes an imaging core configured and arranged for inserting into a distal end of a lumen of a catheter. The imaging core includes at least one transducer mounted to a driveshaft and configured and arranged for transforming applied electrical signals to acoustic signals and also for transforming received echo signals to electrical signals. A motor is coupled to the driveshaft between the one or more transducers and the transformer. The motor includes a rotatable magnet and at least two magnetic field windings disposed around at least a portion of the magnet.

26 Claims, 8 Drawing Sheets

U.S. PATENT DOCUMENTS

| | | |
|---|---|---|
| 5,443,457 A | 8/1995 | Ginn et al. |
| 5,485,846 A | 1/1996 | Webler et al. |
| 5,503,154 A | 4/1996 | Belef |
| 5,596,989 A * | 1/1997 | Morita ............ 600/437 |
| 5,596,991 A | 1/1997 | Tanaka |
| 5,635,784 A * | 6/1997 | Seale ............ 310/90.5 |
| 5,715,825 A | 2/1998 | Crowley |
| 5,749,848 A | 5/1998 | Jang et al. |
| 5,771,895 A | 6/1998 | Slager |
| 5,779,643 A | 7/1998 | Lum et al. |
| 5,842,994 A | 12/1998 | TenHoff et al. |
| 5,916,170 A | 6/1999 | Kolz et al. |
| 5,997,523 A | 12/1999 | Jang |
| 6,010,449 A | 1/2000 | Selmon et al. |
| 6,013,033 A | 1/2000 | Berger et al. |
| 6,074,362 A | 6/2000 | Jang et al. |
| 6,078,831 A | 6/2000 | Belef et al. |
| 6,162,179 A | 12/2000 | Moore |
| 6,165,127 A | 12/2000 | Crowley |
| 6,171,234 B1 | 1/2001 | White et al. |
| 6,261,246 B1 | 7/2001 | Pantages et al. |
| 6,413,222 B1 | 7/2002 | Pantages et al. |
| 6,459,921 B1 | 10/2002 | Belef et al. |
| 6,482,162 B1 | 11/2002 | Moore |
| 6,529,760 B2 | 3/2003 | Pantages et al. |
| 6,592,520 B1 | 7/2003 | Peszynski et al. |
| 6,658,279 B2 | 12/2003 | Swanson et al. |
| 6,733,457 B2 | 5/2004 | Flesch et al. |
| 6,758,818 B2 | 7/2004 | Pantages et al. |
| 6,796,945 B2 | 9/2004 | Belef et al. |
| 6,814,727 B2 | 11/2004 | Mansouri-Ruiz |
| 6,866,635 B2 | 3/2005 | Flesch et al. |
| 6,945,938 B2 | 9/2005 | Grunwald |
| 6,966,891 B2 | 11/2005 | Ookubo et al. |
| 7,245,959 B1 | 7/2007 | Wasicek |
| 7,289,842 B2 | 10/2007 | Maschke |
| 7,306,561 B2 | 12/2007 | Sathyanarayana |
| 7,376,455 B2 | 5/2008 | Crowley et al. |
| 7,396,332 B2 | 7/2008 | Taimisto et al. |
| 7,530,953 B2 | 5/2009 | Harshman et al. |
| 7,544,166 B2 | 6/2009 | Yuan et al. |
| 7,666,143 B2 | 2/2010 | Wilser et al. |
| 7,678,056 B2 | 3/2010 | Wilser et al. |
| 2001/0021841 A1 | 9/2001 | Webler et al. |
| 2001/0029337 A1 | 10/2001 | Pantages et al. |
| 2002/0072704 A1 | 6/2002 | Mansouri-Ruiz |
| 2002/0087081 A1* | 7/2002 | Serrano et al. ............ 600/459 |
| 2002/0151799 A1 | 10/2002 | Pantages et al. |
| 2002/0156515 A1 | 10/2002 | Jang et al. |
| 2002/0188189 A1 | 12/2002 | Belef et al. |
| 2003/0097072 A1 | 5/2003 | Serrano et al. |
| 2003/0105509 A1 | 6/2003 | Jang et al. |
| 2003/0114744 A1 | 6/2003 | Pantages et al. |
| 2004/0030220 A1 | 2/2004 | Hamm |
| 2004/0106866 A1 | 6/2004 | Ookubo et al. |
| 2004/0199047 A1 | 10/2004 | Taimisto et al. |
| 2005/0015011 A1 | 1/2005 | Liard et al. |
| 2005/0043618 A1 | 2/2005 | Mansouri-Ruiz |
| 2005/0101859 A1 | 5/2005 | Maschke |
| 2005/0231063 A1 | 10/2005 | Knorre |
| 2005/0288582 A1 | 12/2005 | Yu et al. |
| 2006/0100522 A1 | 5/2006 | Yuan et al. |
| 2006/0173348 A1 | 8/2006 | Wilser et al. |
| 2006/0173350 A1 | 8/2006 | Yuan et al. |
| 2006/0235299 A1 | 10/2006 | Martinelli |
| 2006/0237652 A1 | 10/2006 | Kimchy et al. |
| 2006/0253028 A1 | 11/2006 | Lam et al. |
| 2006/0263890 A1* | 11/2006 | DeCoster et al. ............ 436/86 |
| 2006/0282153 A1 | 12/2006 | Jang |
| 2007/0016054 A1 | 1/2007 | Cao et al. |
| 2007/0038111 A1 | 2/2007 | Rehrig et al. |
| 2007/0066900 A1 | 3/2007 | O'Keeffe |
| 2007/0167804 A1 | 7/2007 | Park et al. |
| 2007/0167813 A1 | 7/2007 | Lee et al. |
| 2007/0167821 A1 | 7/2007 | Lee et al. |
| 2007/0167824 A1 | 7/2007 | Lee et al. |
| 2007/0167825 A1 | 7/2007 | Lee et al. |
| 2007/0167826 A1 | 7/2007 | Lee et al. |
| 2007/0178717 A1 | 8/2007 | Harshman et al. |
| 2007/0178767 A1 | 8/2007 | Harshman et al. |
| 2007/0178768 A1 | 8/2007 | Harshman et al. |
| 2007/0232893 A1 | 10/2007 | Tanioka |
| 2007/0239253 A1 | 10/2007 | Jagger et al. |
| 2007/0282197 A1 | 12/2007 | Bill et al. |
| 2008/0009746 A1 | 1/2008 | Forster et al. |
| 2008/0177138 A1 | 7/2008 | Courtney et al. |
| 2008/0269615 A1 | 10/2008 | Taimisto et al. |
| 2008/0275304 A1 | 11/2008 | Barbato |
| 2008/0283771 A1 | 11/2008 | Li |
| 2008/0287790 A1 | 11/2008 | Li |
| 2008/0287803 A1 | 11/2008 | Li et al. |
| 2008/0287805 A1 | 11/2008 | Li |
| 2009/0131798 A1 | 5/2009 | Minar et al. |
| 2009/0163818 A1 | 6/2009 | Zelenka et al. |
| 2009/0203991 A1 | 8/2009 | Papaioannou |
| 2009/0264769 A1 | 10/2009 | Sadaka |
| 2009/0275838 A1 | 11/2009 | Marshall et al. |
| 2009/0292204 A1 | 11/2009 | Pansky |
| 2009/0306518 A1 | 12/2009 | Kurse et al. |
| 2010/0036258 A1 | 2/2010 | Dietz et al. |
| 2010/0063398 A1 | 3/2010 | Halmann et al. |
| 2010/0145310 A1 | 6/2010 | Lee et al. |
| 2010/0249599 A1 | 9/2010 | Hastings et al. |
| 2010/0249603 A1 | 9/2010 | Hastings et al. |
| 2010/0249604 A1 | 9/2010 | Hastings et al. |
| 2011/0071400 A1 | 3/2011 | Hastings et al. |
| 2011/0071401 A1 | 3/2011 | Hastings et al. |

FOREIGN PATENT DOCUMENTS

| | | |
|---|---|---|
| DE | 10 2004 042927 | 3/2006 |
| EP | 0216998 | 4/1987 |
| EP | 0557127 | 8/1993 |
| EP | 1026982 | 8/2000 |
| EP | 1143856 | 7/2004 |
| EP | 1363540 | 9/2006 |
| EP | 1707123 A1 | 10/2006 |
| EP | 1707123 B1 | 6/2008 |
| JP | 7000395 | 1/1995 |
| JP | 07/289550 | 11/1995 |
| JP | 09/047455 | 2/1997 |
| WO | 92/03095 | 3/1992 |
| WO | 92/16147 | 10/1992 |
| WO | 94/00052 | 1/1994 |
| WO | 94/16625 | 8/1994 |
| WO | 95/32539 | 11/1995 |
| WO | 96/11634 | 4/1996 |
| WO | 97/17898 | 5/1997 |
| WO | 97/28743 | 8/1997 |
| WO | 99/08596 | 2/1999 |
| WO | 99/08597 | 2/1999 |
| WO | 99/16347 | 4/1999 |
| WO | 99/40853 | 4/1999 |
| WO | 00/07500 | 2/2000 |
| WO | 00/18463 | 4/2000 |
| WO | 00/33741 | 6/2000 |
| WO | 01/68173 | 9/2001 |
| WO | 01/78821 | 10/2001 |
| WO | 02/053034 | 7/2002 |
| WO | 02/069806 | 9/2002 |
| WO | 03/103501 | 12/2003 |
| WO | 03/103502 | 12/2003 |
| WO | 2004/014233 | 2/2004 |
| WO | 2004/042546 | 5/2004 |
| WO | 2006000259 | 1/2006 |
| WO | 2006/113857 | 10/2006 |
| WO | 2007/025230 | 3/2007 |
| WO | 2007/090066 | 8/2007 |
| WO | 2009/094341 | 7/2009 |
| WO | 2009/129438 | 10/2009 |
| WO | 2009/137403 | 11/2009 |
| WO | 2009/141690 | 11/2009 |
| WO | 2009137659 | 11/2009 |
| WO | 2009/149315 | 12/2009 |

OTHER PUBLICATIONS

Long-Sheng Fan et al.; IC-Processed Electrostatic Micro-motors; 19881211; 19881211-19881214; Dec. 11, 1988, pp. 666-669.

International Search Report and Written Opinion for International Application No. PCT/US2010/028439, mailed on Sep. 6, 2010.
International Search Report and Written Opinion for International Application No. PCT/US2010/028440, mailed on Nov. 19, 2010.
Erbel, R., et al. "IVUS of micromotors for cardiovascular imaging," Min. Invas. Ther. & Allied Technol. 1997: 6:195-198.
International Search Report and Written Opinion for International Application No. PCT/US2010/049392, mailed on Dec. 7, 2010.
Esashi M et al.; "Biomedical Microsystems for Minimally Invasive Diagnosis and Treatment", Proceedings of the IEEE. vol. 92. No. 1, Jan. 2004; pp. 98-114.

Jun Keun Chang et al.; "Development of endovascular microtools", Journal of Micromechanics & Microengineering, Institute of Physics Publishing, vol. 12, No. 6, Nov. 2002, pp. 824-831.

International Search Report and Written Opinion for International Application No. PCT/US2010/028454, mailed on Jun. 8, 2011.

International Search Report and Written Opinion for International Application No. PCT/US2010/049384, mailed Mar. 21, 2011.

* cited by examiner

SYSTEMS AND METHODS FOR MAKING AND USING A MOTOR DISTALLY-POSITIONED WITHIN A CATHETER OF AN INTRAVASCULAR ULTRASOUND IMAGING SYSTEM

TECHNICAL FIELD

The present invention is directed to the area of intravascular ultrasound imaging systems and methods of making and using the systems. The present invention is also directed to intravascular ultrasound systems that include imaging cores distally positioned within catheters, the imaging cores including rotational motors, as well as methods of making and using the imaging cores, motors, and intravascular ultrasound systems.

BACKGROUND

Intravascular ultrasound ("IVUS") imaging systems have proven diagnostic capabilities for a variety of diseases and disorders. For example, IVUS imaging systems have been used as an imaging modality for diagnosing blocked blood vessels and providing information to aid medical practitioners in selecting and placing stents and other devices to restore or increase blood flow. IVUS imaging systems have been used to diagnose atheromatous plaque build-up at particular locations within blood vessels. IVUS imaging systems can be used to determine the existence of an intravascular obstruction or stenosis, as well as the nature and degree of the obstruction or stenosis. IVUS imaging systems can be used to visualize segments of a vascular system that may be difficult to visualize using other intravascular imaging techniques, such as angiography, due to, for example, movement (e.g., a beating heart) or obstruction by one or more structures (e.g., one or more blood vessels not desired to be imaged). IVUS imaging systems can be used to monitor or assess ongoing intravascular treatments, such as angiography and stent placement in real (or almost real) time. Moreover, IVUS imaging systems can be used to monitor one or more heart chambers.

IVUS imaging systems have been developed to provide a diagnostic tool for visualizing a variety is diseases or disorders. An IVUS imaging system can include a control module (with a pulse generator, an image processor, and a monitor), a catheter, and one or more transducers disposed in the catheter. The transducer-containing catheter can be positioned in a lumen or cavity within, or in proximity to, a region to be imaged, such as a blood vessel wall or patient tissue in proximity to a blood vessel wall. The pulse generator in the control module generates electrical pulses that are delivered to the one or more transducers and transformed to acoustic pulses that are transmitted through patient tissue. Reflected pulses of the transmitted acoustic pulses are absorbed by the one or more transducers and transformed to electric pulses. The transformed electric pulses are delivered to the image processor and converted to an image displayable on the monitor.

BRIEF SUMMARY

In one embodiment, a catheter assembly for an intravascular ultrasound system includes a catheter, an imaging core, at least one catheter conductor, and at least one motor conductor. The catheter has a longitudinal length, a distal end, and a proximal end. The catheter includes a lumen extending along the longitudinal length of the catheter from the proximal end to the distal end. The imaging core has a longitudinal length that is substantially less than the longitudinal length of the catheter. The imaging core is configured and arranged for inserting into the lumen to the distal end of the catheter. The imaging core includes a rotatable driveshaft, at least one transducer, a transformer, at least one imaging core, and a motor. The rotatable driveshaft has a distal end and a proximal end. The at least one transducer is mounted to the distal end of the driveshaft and is configured and arranged for transforming applied electrical signals to, acoustic signals and also for transforming received echo signals to electrical signals. The transformer is disposed at the proximal end of the driveshaft. The at least one imaging core conductor couples the at least one transducer to the transformer. The motor is coupled to the driveshaft between the one or more transducers and the transformer. The motor includes a rotatable magnet and at least two magnetic field windings disposed around at least a portion of the magnet. The magnet has a longitudinal axis and an aperture defined along the longitudinal axis of the magnet. The at least one catheter conductor is electrically coupled to the transformer and extends to the proximal end of the catheter. The at least one motor conductor is electrically coupled to the magnetic field windings and extends to the proximal end of the catheter.

In another embodiment, a catheter assembly for an intravascular ultrasound system includes a catheter, an imaging core, at least one catheter conductor, and at least one motor conductor. The catheter has a longitudinal length, a distal end, and a proximal end. The catheter includes a lumen extending along the longitudinal length of the catheter from the proximal end to the distal end. The imaging core has a longitudinal length that is substantially less than the longitudinal length of the catheter and is configured and arranged for inserting into the lumen to the distal end of the catheter. The imaging core includes a motor, at least one transducer, and a mirror. The motor includes a rotatable magnet and at least two magnetic field windings disposed around at least a portion of the magnet. The magnet has a longitudinal axis and an aperture defined along the longitudinal axis of the magnet. The at least one transducer is disposed in the imaging core. The at least one transducer is configured and arranged for transforming applied electrical signals to acoustic signals and also for transforming received echo signals to electrical signals. The at least one transducer is fixed in position such that the at least one transducer does not rotate with the magnet. The mirror is positioned distal to the at least one transducer and is tilted at an angle such that when an acoustic beam is emitted from the at least one transducer to the mirror, the acoustic beam is redirected in a direction that is not parallel the longitudinal axis of the magnet. The rotation of the magnet causes the mirror to rotate. The at least one catheter conductor is electrically coupled to the one or more transducers and extends to the proximal end of the catheter. The at least one motor conductor is electrically coupled to the magnetic field windings and extends to the proximal end of the catheter.

In yet another embodiment, a method for imaging a patient using an intravascular ultrasound imaging system includes inserting a catheter into patient vasculature. The catheter includes an imaging core disposed in a distal portion of a lumen defined in the catheter. The imaging core is electrically coupled to a control module by at least one conductor. The imaging core has a longitudinal axis and includes at least one transducer and a magnet that rotates by application of a current from the control module to at least two magnetic field windings wrapped around at least a portion of the magnet. The rotation of the magnet causes rotation of the at least one transducer. The imaging core is positioned in a region to be imaged. At least one electrical signal is transmitted from the control module to the at least one transducer. At least one electrical signal is transmitted from the control module to the at least two magnetic field windings. At least one acoustic signal is transmitted from the at least one transducer to patient tissue in a direction that is not parallel to the longitudinal axis of the imaging core. At least one echo signal is received from a tissue-boundary between adjacent imaged patient tissue by the imaging core. At least one transformed echo signal is transmitted from the at least one transducer to the control module for processing.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present invention is directed to the area of intravascular ultrasound imaging systems and methods of making and using the systems. The present invention is also directed to intravascular ultrasound systems that include imaging cores distally positioned within catheters, the imaging cores including rotational motors, as well as methods of making and using the imaging cores, motors, and intravascular ultrasound systems.

Suitable intravascular ultrasound ("IVUS") imaging systems include, but are not limited to, one or more transducers disposed on a distal end of a catheter configured and arranged for percutaneous insertion into a patient. Examples of IVUS imaging systems with catheters are found in, for example, U.S. Pat. Nos. 7,306,561; and 6,945,938; as well as U.S. Patent Application Publication Nos. 20060253028; 20070016054; 20070038111; 20060173350; and 20060100522, all of which are incorporated by reference.

Figure 1:
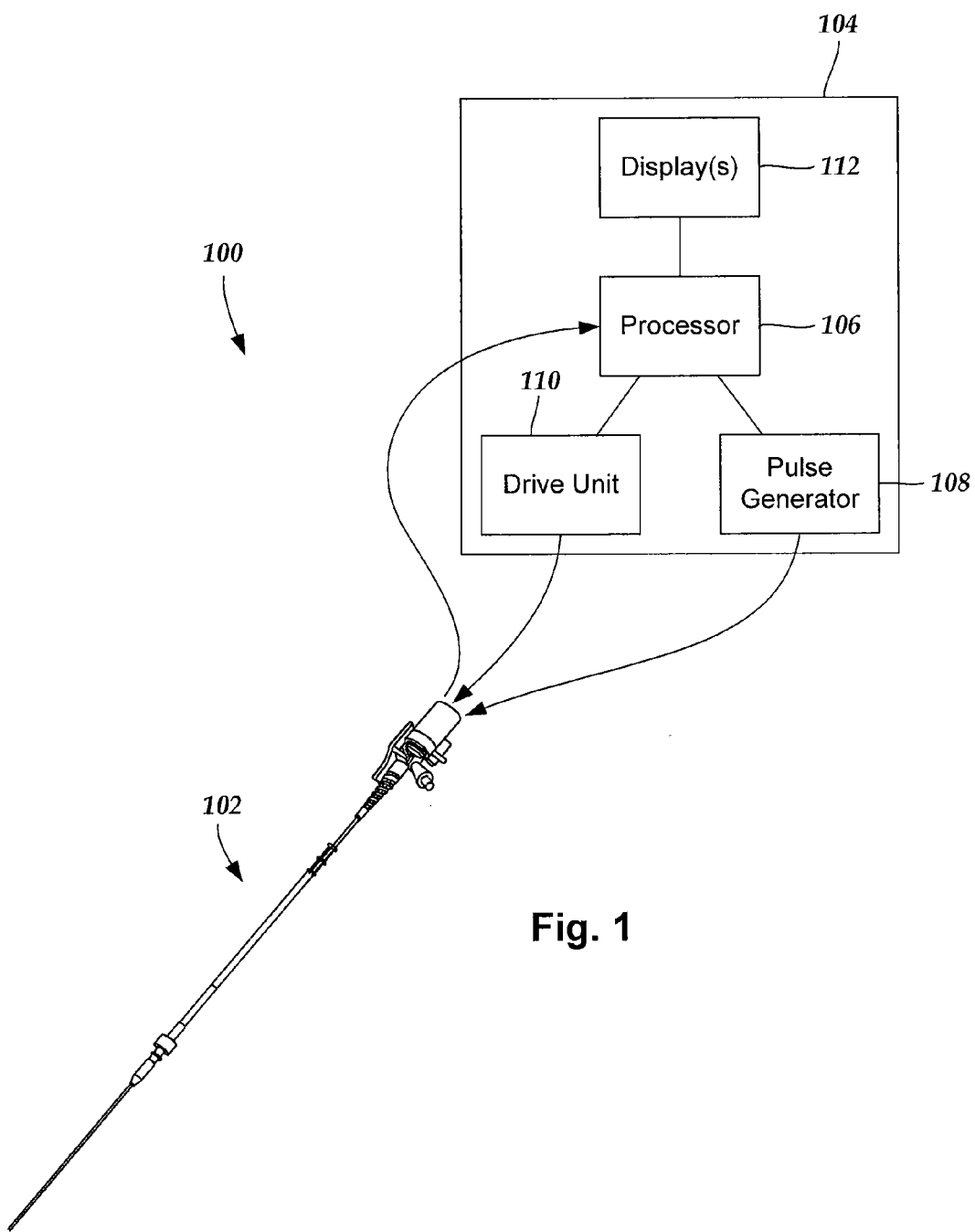
FIG. 1 is a schematic view of one embodiment of an intravascular ultrasound imaging system, according to the invention.

FIG. 1 illustrates schematically one embodiment of an IVUS imaging system 100. The IVUS imaging system 100 includes a catheter 102 that is coupleable to a control module 104. The control module 104 may include, for example, a processor 106, a pulse generator 108, a drive unit 110, and one or more displays 112. In at least some embodiments, the pulse generator 108 forms electric pulses that may be input to one or more transducers (312 in FIG. 3) disposed in the catheter 102. In at least some embodiments, mechanical energy from a pullback motor disposed within the drive unit 110 may be used to provide translational movement of an imaging core (306 in FIG. 3) disposed in the catheter 102.

In at least some embodiments, electric pulses transmitted from the one or more transducers (312 in FIG. 3) may be input to the processor 106 for processing. In at least some embodiments, the processed electric pulses from the one or more transducers (312 in FIG. 3) may be displayed as one or more images on the one or more displays 112. In at least some embodiments, the processor 106 may also be used to control the functioning of one or more of the other components of the control module 104. For example, the processor 106 may be used to control at least one of the frequency or duration of the electrical pulses transmitted from the pulse generator 108, the rotation rate of the imaging core (306 in FIG. 3) by the drive unit 110, the velocity or length of the pullback of the imaging core (306 in FIG. 3) by the drive unit 110, or one or more properties of one or more images formed on the one or more displays 112.

Figure 2:
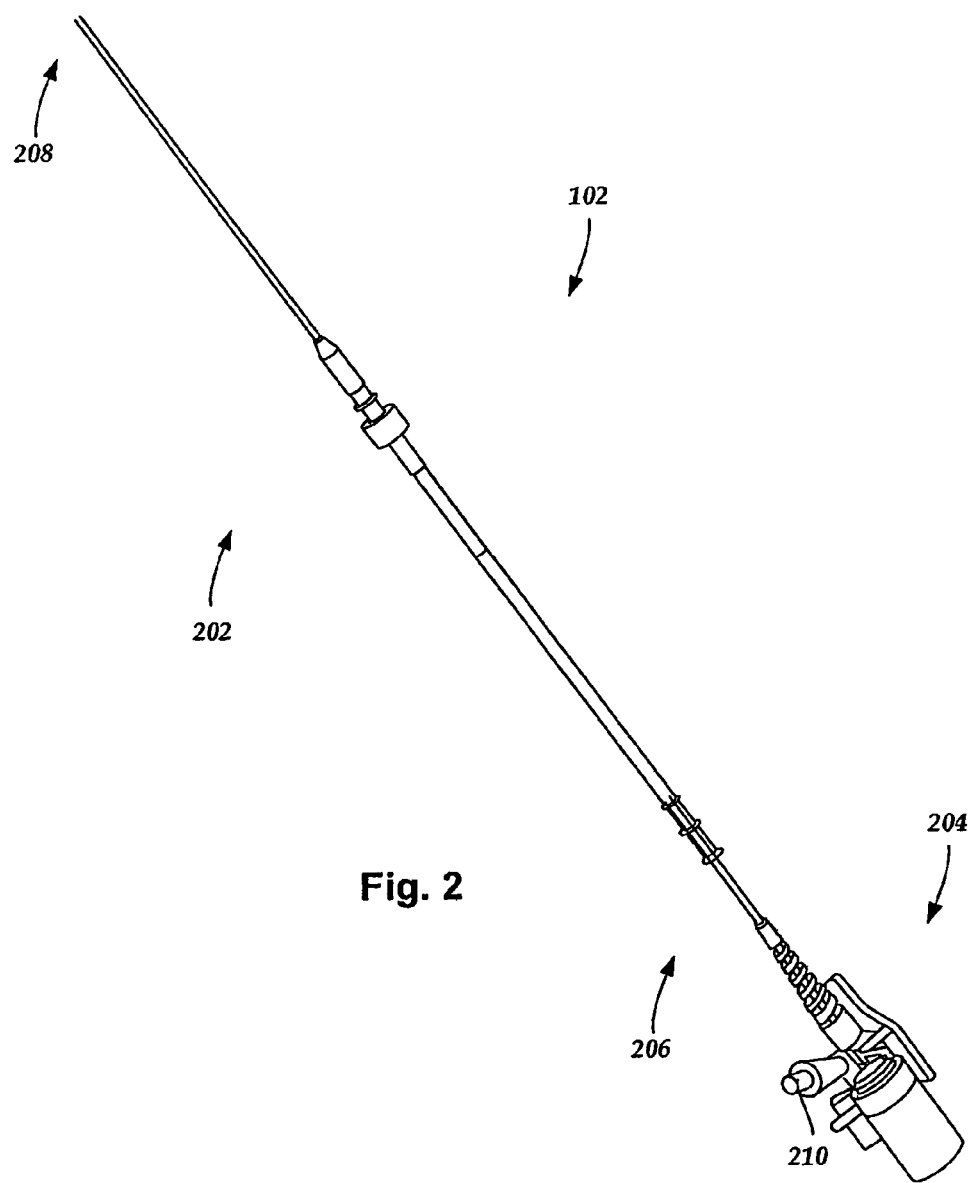
FIG. 2 is a schematic side view of one embodiment of a catheter of an intravascular ultrasound imaging system, according to the invention.

FIG. 2 is a schematic side view of one embodiment of the catheter 102 of the IVUS imaging system (100 in FIG. 1). The catheter 102 includes an elongated member 202 and a hub 204. The elongated member 202 includes a proximal end 206 and a distal end 208. In FIG. 2, the proximal end 206 of the elongated member 202 is coupled to the catheter hub 204 and the distal end 208 of the elongated member is configured and arranged for percutaneous insertion into a patient. In at least some embodiments, the catheter 102 defines at least one flush port, such as flush port 210. In at least some embodiments, the flush port 210 is defined in the hub 204. In at least some embodiments, the hub 204 is configured and arranged to couple to the control module (104 in FIG. 1). In some embodiments, the elongated member 202 and the hub 204 are formed as a unitary body. In other embodiments, the elongated member 202 and the catheter hub 204 are formed separately and subsequently assembled together.

Figure 3:
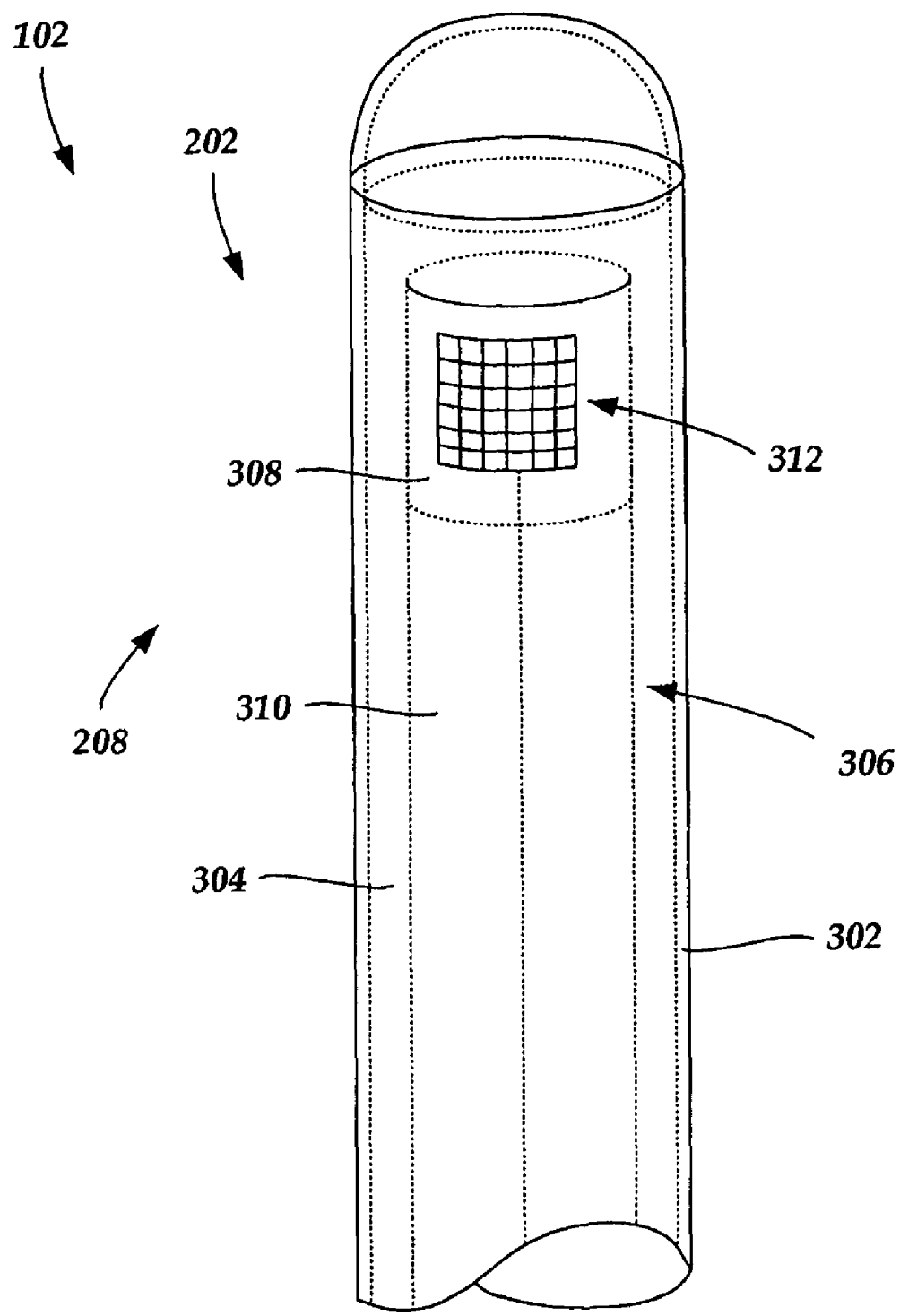
FIG. 3 is a schematic perspective view of one embodiment of a distal end of the catheter shown in FIG. 2 with an imaging core disposed in a lumen defined in the catheter, according to the invention.

FIG. 3 is a schematic perspective view of one embodiment of the distal end 208 of the elongated member 202 of the catheter 102. The elongated member 202 includes a sheath 302 and a lumen 304. An imaging core 306 is disposed in the lumen 304. The imaging core 306 includes an imaging device 308 coupled to a distal end of a rotatable driveshaft 310.

The sheath 302 may be formed from any flexible, biocompatible material suitable for insertion into a patient. Examples of suitable materials include, for example, polyethylene, polyurethane, plastic, spiral-cut stainless steel, nitinol hypotube, and the like or combinations thereof.

One or more transducers 312 may be mounted to the imaging device 308 and employed to transmit and receive acoustic pulses. In a preferred embodiment (as shown in FIG. 3), an array of transducers 312 are mounted to the imaging device 308. In other embodiments, a single transducer may be employed. In yet other embodiments, multiple transducers in an irregular-array may be employed. Any number of transducers 312 can be used. For example, there can be two, three, four, five, six, seven, eight, nine, ten, twelve, fifteen, sixteen, twenty, twenty-five, fifty, one hundred, five hundred, one thousand, or more transducers. As will be recognized, other numbers of transducers may also be used.

The one or more transducers 312 may be formed from one or more known materials capable of transforming applied electrical pulses to pressure distortions on the surface of the one or more transducers 312, and vice versa. Examples of suitable materials include piezoelectric ceramic materials, piezocomposite materials, piezoelectric plastics, barium titanates, lead zirconate titanates, lead metaniobates, polyvinylidenefluorides, and the like.

The pressure distortions on the surface of the one or more transducers 312 form acoustic pulses of a frequency based on the resonant frequencies of the one or more transducers 312. The resonant frequencies of the one or more transducers 312 may be affected by the size, shape, and material used to form the one or more transducers 312. The one or more transducers 312 may be formed in any shape suitable for positioning within the catheter 102 and for propagating acoustic pulses of a desired frequency in one or more selected directions. For example, transducers may be disc-shaped, block-shaped, rectangular-shaped, oval-shaped, and the like. The one or more transducers may be formed in the desired shape by any process including, for example, dicing, dice and fill, machining, microfabrication, and the like.

As an example, each of the one or more transducers 312 may include a layer of piezoelectric material sandwiched between a conductive acoustic lens and a conductive backing material formed from an acoustically absorbent material (e.g., an epoxy substrate with tungsten particles). During operation, the piezoelectric layer may be electrically excited by both the backing material and the acoustic lens to cause the emission of acoustic pulses.

In at least some embodiments, the one or more transducers 312 can be used to form a radial cross-sectional image of a surrounding space. Thus, for example, when the one or more transducers 312 are disposed in the catheter 102 and inserted into a blood vessel of a patient, the one more transducers 312 may be used to form an image of the walls of the blood vessel and tissue surrounding the blood vessel.

In at least some embodiments, the imaging core 306 may be rotated about a longitudinal axis of the catheter 102. As the imaging core 306 rotates, the one or more transducers 312 emit acoustic pulses in different radial directions. When an emitted acoustic pulse with sufficient energy encounters one or more medium boundaries, such as one or more tissue boundaries, a portion of the emitted acoustic pulse is reflected back to the emitting transducer as an echo pulse. Each echo pulse that reaches a transducer with sufficient energy to be detected is transformed to an electrical signal in the receiving transducer. The one or more transformed electrical signals are transmitted to the control module (104 in FIG. 1) where the processor 106 processes the electrical-signal characteristics to form a displayable image of the imaged region based, at least in part, on a collection of information from each of the acoustic pulses transmitted and the echo pulses received.

As the one or more transducers 312 rotate about the longitudinal axis of the catheter 102 emitting acoustic pulses, a plurality of images are formed that collectively form a radial cross-sectional image of a portion of the region surrounding the one or more transducers 312, such as the walls of a blood vessel of interest and the tissue surrounding the blood vessel. In at least some embodiments, the radial cross-sectional image can be displayed on one or more displays (112 in FIG. 1).

In at least some embodiments, the drive unit (110 in FIG. 1) is used to provide translational movement to the imaging core 306 within the lumen of the catheter 102 while the catheter 102 remains stationary. For example, the imaging core 306 may be advanced (moved towards the distal end of the catheter 102) or retracted/pulled back (moved towards the proximal end of the catheter 102) within the lumen 304 of the catheter 102 while the catheter 102 remains in a fixed location within patient vasculature (e.g., blood vessels, the heart, and the like). During longitudinal movement (e.g., pullback) of the imaging core 306, an imaging procedure may be performed, wherein a plurality of cross-sectional images are formed along a longitudinal length of patient vasculature.

In at least some embodiments, the pullback distance of the imaging core is at least 5 cm. In at least some embodiments, the pullback distance of the imaging core is at least 10 cm. In at least some embodiments, the pullback distance of the imaging core is at least 15 cm. In at least some embodiments, the pullback distance of the imaging core is at least 20 cm. In at least some embodiments, the pullback distance of the imaging core is at least 25 cm.

The quality of an image produced at different depths from the one or more transducers 312 may be affected by one or more factors including, for example, bandwidth, transducer focus, beam pattern, as well as the frequency of the acoustic pulse. The frequency of the acoustic pulse output from the one or more transducers 312 may also affect the penetration depth of the acoustic pulse output from the one or more transducers 312. In general, as the frequency of an acoustic pulse is lowered, the depth of the penetration of the acoustic pulse within patient tissue increases. In at least some embodiments, the IVUS imaging system 100 operates within a frequency range of 5 MHz to 60 MHz.

In at least some embodiments, the catheter 102 with one or more transducers 312 mounted to the distal end 208 of the imaging core 306 may be inserted percutaneously into a patient via an accessible blood vessel, such as the femoral artery, at a site remote from the selected portion of the selected region, such as a blood vessel, to be imaged. The catheter 102 may then be advanced through the blood vessels of the patient to the selected imaging site, such as a portion of a selected blood vessel.

It is desirable to have uniform rotation of the imaging core 306 during operation. When the catheter 102 is advanced through blood vessels of the patient, the catheter 102 may navigate one or more tortuous regions or one or more narrow regions which may press against one or more portions of the catheter 102 and cause a non-uniform rotation (e.g., a wobble, a vibration, or the like) of the imaging core 306 during operation. Non-uniform rotation may lead to the distortion of a subsequently-generated IVUS image. For example, the subsequently-generated IVUS image may be blurred.

In conventional systems, a rotational motor is disposed in a proximal portion of the catheter 302 or in a unit to which the proximal portion of the catheter is attached. Due to the distance between a proximally-positioned rotational motor and an imaging core and the tortuous nature of the vasculature into which the distal end of the catheter is positioned during operation, non-uniform rotation can be difficult to prevent.

A motor disposed on the imaging core and positioned in a distal portion of the catheter is described. The imaging core has a longitudinal length that is substantially less than a longitudinal length of the catheter. The imaging core also includes one or more transducers. In at least some embodiments, disposing the motor in the imaging core may reduce, or even eliminate non-uniform rotation caused by one or more off-axis forces (e.g., blood vessel walls pressing against portions of the catheter). In at least some embodiments, the motor includes a rotor formed from a permanent magnet. In at least some embodiments, the catheter has a diameter that is no greater than one millimeter.

It may be the case that the distal end of the catheter 102 is disposed in patient vasculature without having any information regarding the precise location or orientation of the one or more transducers. In at least some embodiments, a sensing device may be disposed in the imaging core for sensing the location or orientation of the one or more transducers. In at least some embodiments, the sensing device includes one or more magnetic sensors. In some embodiments, the sensing device includes a plurality of magnetic sensors located external to the patient. In other embodiments, one or more sensors are positioned within the patient, and a plurality of sensors are positioned external to the patient.

Additionally or alternatively, in at least some embodiments, the sensing device measures the amplitude or orientation of the rotating magnet magnetization vector produced by the motor. In at least some embodiments, data from the magnetic sensing device may be input to a drive circuit to provide controlled and uniform rotation of the imaging core (e.g., through a feedback loop). In at least some embodiments, data from the sensing device may also be used to make corrections to data collected during non-uniform rotation of the imaging core.

Figure 4:
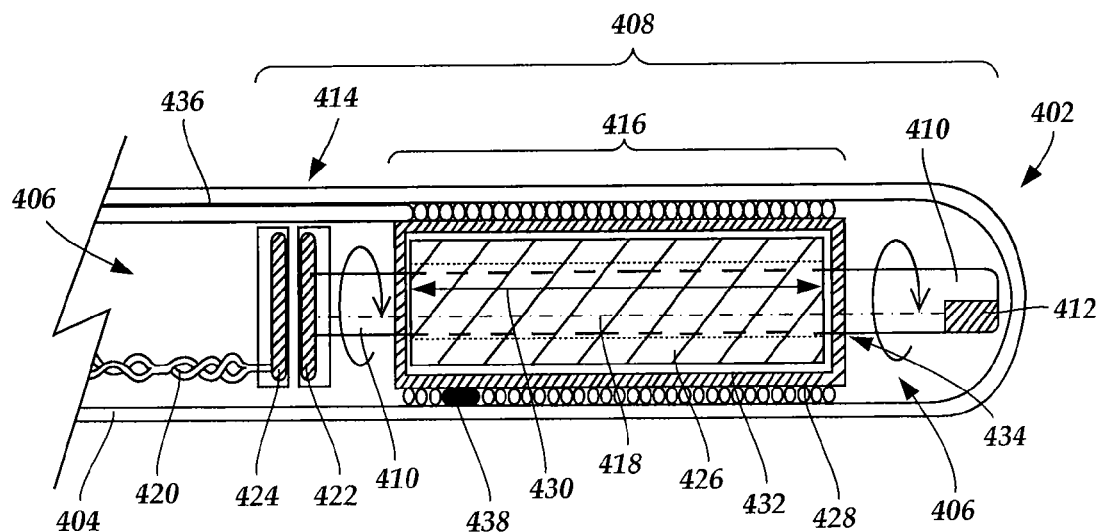
FIG. 4 is a schematic longitudinal cross-sectional view of one embodiment of a distal end of a catheter, the distal end of the catheter including an imaging core with a motor, a transformer, and one or more rotating transducers, according to the invention.

FIG. 4 is a schematic longitudinal cross-sectional view of one embodiment of a distal end of a catheter 402. The catheter 402 includes a sheath 404 and a lumen 406. A rotatable imaging core 408 is disposed in the lumen 406 at the distal end of the catheter 402. The imaging core 408 includes a rotatable driveshaft 410 with one or more transducers 412 coupled to a distal end of the driveshaft 410 and a transformer 414 coupled to a proximal end of the driveshaft 410. The imaging core 408 also includes a motor 416 coupled to the driveshaft 410. One or more imaging core conductors 418 electrically couple the one or more transducers 412 to the transformer 414. In at least some embodiments, the one or more imaging core conductors 418 extend within the driveshaft 410. One or more catheter conductors 420 electrically couple the transformer 414 to the control module (104 in FIG. 1). In at least some embodiments, the one or more of the catheter conductors 420 may extend along at least a portion of the longitudinal length of the catheter 402 as shielded electrical cables, such as a coaxial cable, or a twisted pair cable, or the like.

When the catheter 402 employs one or more rotatable transducers 412, the transformer 414 is typically used to electrically couple the stationary portions of the system (e.g., the control module (104 in FIG. 1)) with the rotating portions of the system (e.g., the one or more transducers 412). In conventional systems employing a rotating transducer, the transformer is positioned at a proximal end of a catheter (such as catheter hub 204 in FIG. 2). Typically, the transformer 414 employs inductive coupling between a rotating component and a stationary component (e.g., a rotor and a stator, or a rotating pancake coil and a stationary pancake coil, or the like). Pulses of current from the control module (104 in FIG. 1) may be induced in the rotating component, via the stationary component. The induced current may transmit to the one or more transducers and may be transformed to an acoustic signal and emitted as one or more acoustic pulses. Echo pulses received by the one or more transducers may be transformed to electrical signals and transmitted to the rotating component. A voltage may be induced in the stationary component by the electrical signal in the rotating component. In at least some embodiments, the voltage may be input to the control module (104 in FIG. 1) for processing.

The transformer 414 is disposed on the imaging core 408. In at least some embodiments, the transformer 414 includes a rotating component 422 coupled to the driveshaft 410 and a stationary component 424 disposed spaced apart from the rotating component 414. In some embodiments, the stationary part 424 is proximal to, and immediately adjacent to, the rotating component 422. The rotating component 422 is electrically coupled to the one or more transducers 412 via the one or more imaging core conductors 418 disposed in the imaging core 408. The stationary component 416 is electrically coupled to the control module (104 in FIG. 1) via one or more conductors 420 disposed in the lumen 406. Current is inductively passed between the rotating component 422 and the stationary component 424 (e.g., a rotor and a stator, or a rotating pancake coil and a stationary pancake coil, or the like).

In at least some embodiments, the transformer 414 is positioned at a proximal end of the imaging core 408. In at least some embodiments, the components 422 and 424 of the transformer 414 are disposed in a ferrite form. In at least some embodiments, the components 422 and 424 are smaller in size than components conventionally positioned at the proximal end of the catheter. Additionally, the diameter of the wire 418 used to form the components 422 and 424 may be smaller in size than the diameter of wire used in conventional components. In at least some embodiments, the diameter of wire 418 is no greater than 0.004 inches (0.010 cm). In at least some embodiments, the diameter of the wire is no greater than 0.003 inches (0.008 cm). In at least some embodiments, the diameter of the wire is no greater than 0.002 inches (0.005 cm).

Additionally, the length of the wire 418 used to couple the rotating component 422 to the one or more transducers 412 may be less than for conventional components because the component 422 is typically positioned in closer proximity to the one or more transducers 412 than with conventional systems. Thus, the resistance of the wire 418 used to form the rotating component 422 and to couple to the one or more transducers 412 may be less than for conventional systems. Accordingly, the inductance and mutual inductance of the components 422 and 424 may need to be adjusted by increasing the number of turns of the components 422 and 424 compared to conventional coils.

The motor 416 includes a rotor 426 and a stator 428. In at least some embodiments, the rotor 426 is a permanent magnet with a longitudinal axis, indicated by a two-headed arrow 430, which is coaxial with the longitudinal axis of the imaging core 408 and the driveshaft 410. The magnet 426 may be formed from many different magnetic materials suitable for implantation including, for example, neodymium-iron-boron, or the like. One example of a suitable neodymium-iron-boron magnet is available through Hitachi Metals America Ltd, San Jose, Calif.

In at least some embodiments, the magnet 426 is cylindrical. In at least some embodiments, the magnet 426 has a magnetization M of no less than 1.4 T. In at least some embodiments, the magnet 426 has a magnetization M of no less than 1.5 T. In at least some embodiments, the magnet 426 has a magnetization M of no less than 1.6 T. In at least some embodiments, the magnet 426 has a magnetization vector that is perpendicular to the longitudinal axis of the magnet 426. In at least some embodiments, the magnet 426 is disposed in a housing 432.

In at least some embodiments, the magnet 426 is coupled to the driveshaft 410 and is configured and arranged to rotate the driveshaft 410 during operation. In at least some embodiments, the magnet 426 defines an aperture 434 along the longitudinal axis 430 of the magnet 426. In at least some embodiments, the driveshaft 410 and the one or more imaging core conductors 418 extend through the aperture 434. In at least some other embodiments, the drive shaft 410 is discontinuous and, for example, couples to the magnet 426 at opposing ends of the magnet 426. In which case, the one or more imaging core conductors 418 still extend through the aperture 434. In at least some embodiments, the magnet 426 is, coupled to the driveshaft 410 by an adhesive. Alternatively, in some embodiments the driveshaft 410 and the magnet 426 can be machined from a single block to magnetic material with the aperture 434 drilled down a length of the driveshaft 410 for receiving the imaging core conductors 418.

In at least some embodiments, the stator 428 includes two perpendicularly-oriented magnetic field windings (502 and 504 in FIG. 5) which provide a rotating magnetic field to produce torque causing rotation of the magnet 426. The stator 428 is provided with power from the control module (104 in FIG. 1) via one or more motor conductors 436.

In at least some embodiments, a sensing device 438 is disposed on the imaging core 408. In at least some embodiments, the sensing device 438 is coupled on the housing 432. In at least some embodiments, the sensing device 438 is configured and arranged to measure the amplitude of the magnetic field in a particular direction. In at least some embodiments, the sensing device 438 uses at least some of the measured information to sense the angular position of the magnet 426. In at least some embodiments, at least some of the measured information obtained by the sensing device 438 is used to control the current provided to the stator 428 by the one or more motor conductors 436.

In at least some embodiments, the diameter of the catheter 402 is no greater than 0.042 inches (0.11 cm). In at least some embodiments, the diameter of the catheter 402 is no greater than 0.040 inches (0.11 cm). In at least some embodiments, the diameter of the catheter 402 is no greater than 0.038 inches (0.10 cm). In at least some embodiments, the diameter of the catheter 402 is no greater than 0.036 inches (0.09 cm). In at least some embodiments, the diameter of the catheter 402 is no greater than 0.034 inches (0.09 cm). In at least some embodiments, the diameter of the catheter 402 is sized to accommodate intracardiac echocardiography systems.

In at least some embodiments, the diameter of the magnet 426 is no greater than 0.025 inches (0.06 cm). In at least some embodiments, the diameter of the magnet 426 is no greater than 0.022 inches (0.06 cm). In at least some embodiments, the diameter of the magnet 426 is no greater than 0.019 inches (0.05 cm). In at least some embodiments, the diameter of the aperture 434 is no greater than 0.010 inches (0.03 cm). In at least some embodiments, the diameter of the aperture 434 is no greater than 0.009 inches (0.02 cm). In at least some embodiments, the diameter of the aperture 434 is no greater than 0.008 inches (0.02 cm). In at least some embodiments, the longitudinal length of the magnet 426 is no greater than 0.13 inches (0.33 cm). In at least some embodiments, the longitudinal length of the magnet 426 is no greater than 0.12 inches (0.30 cm). In at least some embodiments, the longitudinal length of the magnet 426 is no greater than 0.11 inches (0.28 cm).

In at least some embodiments, the motor 416 provides enough torque to rotate the one or more transducers 412 at a frequency of at least 15 Hz. In at least some embodiments, the motor 416 provides enough torque to rotate the one or more transducers 412 at a frequency of at least 20 Hz. In at least some embodiments, the motor 416 provides enough torque to rotate the one or more transducers 412 at a frequency of at least 25 Hz. In at least some embodiments, the motor 416 provides enough torque to rotate the one or more transducers 412 at a frequency of at least 30 Hz. In at least some embodiments, the motor 416 provides enough torque to rotate the one or more transducers 412 at a frequency of at least 35 Hz. In at least some embodiments, the motor 416 provides enough torque to rotate the one or more transducers 412 at a frequency of at least 40 Hz.

In a preferred embodiment, the torque is about the longitudinal axis 430 of the magnet 426 so that the magnet 426 rotates. In order for the torque of the magnet 426 to be about the longitudinal axis 430, the magnetic field of the magnetic field windings (i.e., coils of the stator) lies in the plane perpendicular to the longitudinal axis 430, with the field vector rotating about the longitudinal axis 430.

Figure 5:
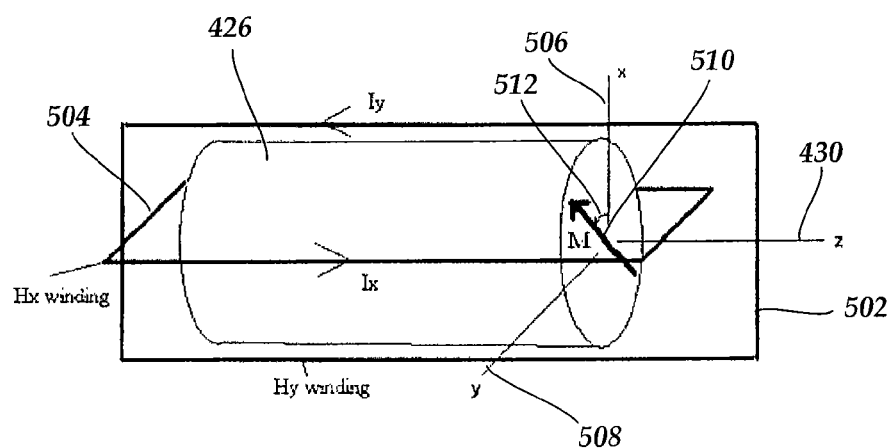
FIG. 5 is a schematic perspective view of one embodiment of a rotating magnet and associated windings, according to the invention.

As discussed above, the stator 428 provides a rotating magnetic field to produce a torque the rotor 426. The stator 428 may comprise two perpendicularly-oriented magnetic field windings ("windings") that wrap around the magnet 426 as one or more turns to form a rotating magnetic field. FIG. 5 is a schematic perspective view of one embodiment of the rotating magnet 426 and windings, represented as orthogonal rectangular boxes 502 and 504. Although the windings 502 and 504 are shown as two orthogonal rectangles, it will be understood that the each of the windings 502 and 504 may represent multiple turns of wire which may be spread out to minimize an increase in the diameter of the catheter (402 in FIG. 4). When the windings 502 and 504 are spread out, a band of current may be generated instead of the lines of current shown in FIG. 5.

In at least some embodiments, the diameter of the wire used to form the windings 502 and 504 is no greater than 0.004 inches (0.010 cm). In at least some embodiments, the diameter of the wire is no greater than 0.003 inches (0.008 cm). In at least some embodiments, the diameter of the wire is no greater than 0.002 inches (0.005 cm).

In order for the magnet 426 to rotate about the longitudinal axis 430, the torque must be about the longitudinal axis 430. Therefore, the magnetic field generated by the windings 502 and 504 must lie in a plane perpendicular to the longitudinal axis 430 with a magnetic field vector H for the windings 502 and 504 rotating about the longitudinal (z) axis 430 to torque and rotate the magnet 426. FIG. 5 also shows an x-axis 506 and a y-axis 508 that are orthogonal to each other and to the longitudinal axis 430. As shown in FIG. 5, the magnetization vector M 510 of the magnet 402 is in an x-y plane that is perpendicular to the longitudinal axis 430.

The winding 502 produces a magnetic field at the center of the winding 502 that is parallel to the y-axis 508. The winding 504 produces a magnetic field at the center of the winding 504 that is parallel to the x-axis 506. The combined magnetic field vector H for the windings 502 and 504 is given by:

$$H = H_x x' + H_y y'.$$

where x' and y' are unit vectors in the x and y directions, respectively. The magnetization vector M rotates through the angle 512, which is equal to the angular velocity of the magnet 426 times the elapsed time for uniform rotation. Thus, the magnetization vector M is given by:

$$M = M(\cos(\omega t) x' + \sin(\omega t) y').$$

The magnetic moment vector m is given by:

$$m = MV;$$

where M=magnetization vector of the magnet 426 in Tesla; and V=the magnet 426 volume in m³.

The torque τ exerted on the magnet 426 is given by:

$$\tau = m \times H;$$

where τ=the torque vector in N–m; m=the magnetic moment vector in Tesla-m³; H=the magnetic field vector of the windings 502 and 504 in amp/m; and x=the vector cross product.

The vector cross product can be evaluated:

$$\tau = MV(H_y \cos(\omega t) - H_x \sin(\omega t)) z'.$$

The vector cross product verifies that the torque produced by the windings 502 and 504 on the magnetic moment vector m is indeed about the longitudinal axis 430. Moreover, the torque will be uniform and independent of time if the magnetic fields generated by the field windings 502 and 504 are given by:

$$H_x = -H \sin(\omega t);$$

$$H_y = H \cos(\omega t);$$

thereby yielding a torque τ given by:

$$\tau = MVHz'.$$

The torque is uniform because the magnetic field is uniformly rotating, since $H^2 = H_x^2 + H_y^2$ is independent of time, and the $H_x$ and $H_y$ components describe clockwise rotation of the winding magnetic field vector H about the z' axis. The resulting uniform torque on a symmetric magnet having the magnetization vector M in the x-y plane is an inherent expression of a rotating field electric motor.

Thus, the orthogonal fields produce a magnetic field that uniformly rotates about the longitudinal axis 430 at angular speed ω. Under operational conditions, the magnetization vector M of the magnet 426 will follow the winding magnetic field vector H of the windings 502 and 504 with a slip angle that is determined by a system drag torque. When the angular speed ω is increased, the drag torque (and the slip angle) increases until the magnet 426 can no longer rotate fast enough to keep up with the magnetic field.

A changing slip angle may potentially lead to non-uniform rotation. In at least some embodiments, the sensing device 438 facilitates maintaining uniform rotation of the magnet 426 by maintaining a uniformly rotating magnetic field. In at least some embodiments, the sensing device 438 controls the currents that produce $H_x$ and $H_y$ by feedback from measured values for $M_x$ and $M_y$ components. The relationship between $H_x$ and $H_y$ and $M_x$ and $M_y$ is given by:

$$H_x \propto I_x \propto -M_y;\ \text{and}$$

$$H_y \propto I_y \propto M_x;$$

where $I_x$=the current in amps producing the magnetic field component $H_x$; and $I_y$=the current in amps producing the magnetic field component $H_y$.

In at least some embodiments, the sensing device 438 may be implemented in digital form. In at least some embodiments, digitally processed data output from the sensing device 438 is used to compute the currents at each point in time to maintain uniform rotation. In at least some embodiments, the digital sensing device 438 may measure more than one component of the magnetic field of the magnet 426 at a given point to fully determine the currents for a given rotational direction.

In at least some other embodiments, the sensing device 438 may be implemented in analog form. In at least some embodiments, the analog sensing device 438 includes two magnetic sensors placed 90 degrees apart on the housing (432 in FIG. 4) or elsewhere on the imaging core (408 in FIG. 4). Generally, the magnetic field generated by the magnet 426 is substantially larger than the magnetic field generated by the windings 502 and 504. Thus, the sensors of the sensing device 438 measure the perpendicular components of the magnetization vector M in the x-y plane, relative to the axes passing from the center of the magnet 426 to the sensors. The measured signals can be amplified and fed back to the currents in the windings 502 and 504. If, as shown in the previous equations, the x current is inverted, the magnet 426 rotates clockwise. If the y current is inverted, the magnet 426 rotates counterclockwise.

In at least some embodiments, the sensing device 438 includes at least some magnetic sensors located external to the patient. For example, two tri-axial magnetic sensors, including six individual sensors, may measure the x, y, and z components of a rotating magnetic field of the magnet 426 at two locations external to the patient. In at least some embodiments, magnetic field sensing of the rotating magnet 426 is facilitated by sensing only magnetic fields that rotate in phase with the magnet winding drive currents. Data from the external sensors may be inverted to find the x, y, and z coordinates of the rotating magnet (and IVUS transducer), and the spatial orientation of the magnet 426. This data can be used to form a three dimensional image of surrounding tissue (e.g., bends in an artery) during pull back imaging.

In at least some embodiments, one or more sensors may be positioned in proximity to the rotating magnet 426 and implantable into the patient, while a plurality of sensors remain external to the patient. The implantable sensor may identify the angular orientation of the rotating magnet 426, and this data may be used to accept only data from the external sensors that have the proper frequency and proper phase angle of the rotating magnet while rejecting data obtained from external sensors with an improper frequency and phase angle, thereby further increasing the signal-to-noise ratio in the external sensor data.

The amount of magnetic torque that may be generated by the motor 416 may be limited by the amount of current that may be passed through the windings 502 and 504 without generating excessive heat in the catheter (402 in FIG. 4). Heat is generated in the windings 502 and 504 by Joule heating at a rate given by:

$$P = I^2 R;$$

where P=the power dissipated as heat in watts; R=the resistance of the windings 502 and 504; and I=the amplitude of the current in amps.

The value for P is divided by two because sinusoidal current is employed. However the value for P is also multiplied by two because there are two windings 502 and 504. In at least one experiment, it has been estimated that up to 300 mW of heat is readily dissipated in blood or tissue without perceptibly increasing the temperature of the motor (416 in FIG. 4). In at least one experiment, it has been estimated that heat dissipation increases to several watts when blood is flowing.

The magnetic field H of the windings 502 and 504 having N turns and inputting current I may be computed. The result follows from the formula for the magnetic field generated by a current-carrying line segment. Typically, the lengths of the long ends of the rectangular-shaped windings 502 and 504 parallel with the longitudinal axis 430 are substantially greater than the lengths of the short ends of the windings 502 and 504. Accordingly, the short ends may not significantly contribute to the magnetic torque. The magnetic field H of the windings 502 and 504 having N turns and inputting current I is given by:

$$H = 2NI/(\pi D \sqrt{(1+(D/L)^2)});$$

where N=the number of turns of the windings 502 and 504; D=the winding width in meters (typically the diameter of the housing (432 in FIG. 4); and L=the length of the windings 502 and 504 in meters. NI can be analyzed in terms of the power dissipated in the windings 502 and 504. Although theoretical optimization of all parameters is possible, safety limits may be incorporated into design implementation.

In one exemplary embodiment, rectangular windings 502 and 504 have 8 turns of silver wire with a 2.7 inches (6.86 cm) length, a 0.002 inch (0.005 cm) diameter, and a resistance of 0.5 Ohms. A magnet 426 has a cylindrical shape with an outer diameter of 0.022 inches (0.056 cm), an inner diameter of 0.009 inches (0.022 cm), and a longitudinal length of 0.132 inches (0.34 cm). The magnetization M=1.4 for the magnet 426 having the above-mentioned dimensions formed from neodymium-iron-boron. The maximum power P is equal to 0.3 watts, the maximum current amplitude is 0.77 amps, and the quantity NI is 6.2 amps. Using the above-mentioned values, the torque on the magnet 426 is given by:

$$\tau = 2MV(NI)/(\pi D \sqrt{(1+(D/L)^2)}).$$

Inserting the above-mentioned values gives a torque of 4 μN-m=0.4 gm-mm, which is approximately four times larger than an estimated maximum frictional drag on the magnet 426. The corresponding force is about 0.1 gram, or about 30 times the weight of the magnet 426. Although torque may be increased by increasing the magnet radius, it is desirable that the catheter (402 in FIG. 4) be small enough to be disposed in a wide variety of patient vasculature. Additional considerations for insertion of the catheter into patient vasculature may be considered including, for example, the length of the imaging core (408 in FIG. 4) (because the relative stiffness of the imaging core (408 in FIG. 4) may affect maneuverability of the catheter), heat generation, the resistivity of metals at room temperature, and the strength of the materials used to form the magnet 426.

It may be difficult to form the windings 502 and 504. For example, it may be difficult to wind a wire of 0.002 inch (0.005 cm) diameter around a cylindrical surface of a housing (432 in FIG. 4). In at least some embodiments, the windings 502 and 504 are deposited onto a thin film (e.g., a polyimide film, or the like), which is then disposed onto the housing (432 in FIG. 4). For example, one or more types of metals (e.g., copper, silver, gold, or other metals or metal alloys) are deposited onto the thin film, and the thin film is disposed onto the housing (e.g., using one or more adhesives or other types of suitable coupling methods). In alternate embodiments, the housing (432 in FIG. 4) is formed from a ceramic cylinder or extruded polyimide tube, or other material that is suitable for deposition of metal strip lines. A three-dimensional lithography process may be used to deposit and define the windings 502 and 504 on the cylinder. For example, a metal film may be deposited uniformly on an outer surface of the cylinder and a laser may be used to remove undesired metal film from the outer surface of the cylinder, thereby defining the windings 502 and 504.

Figure 6:
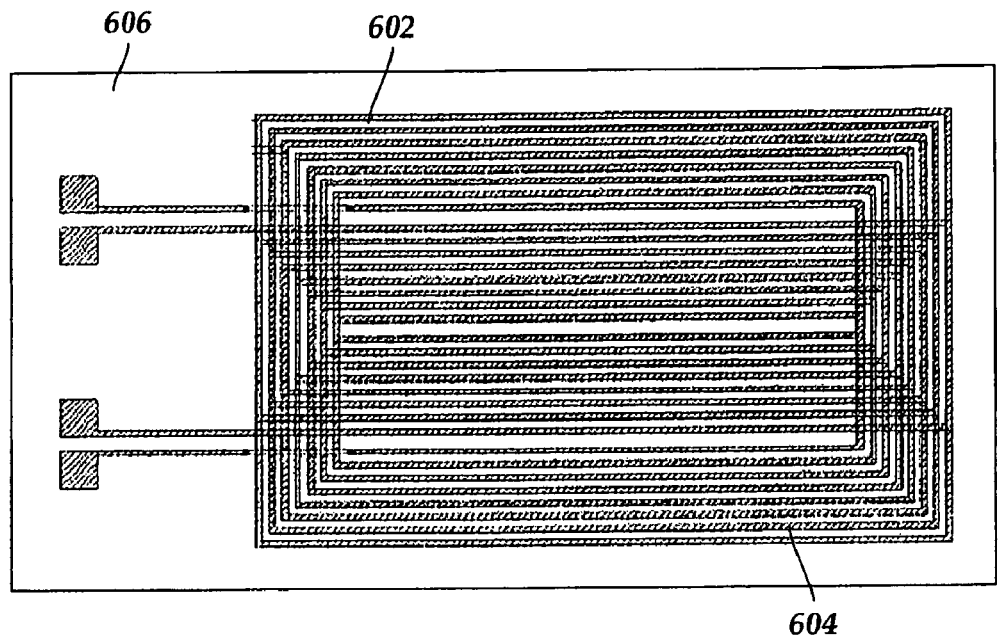
FIG. 6 is a schematic top view of one embodiment of windings disposed on a thin film, according to the invention.

FIG. 6 is a schematic top view of one embodiment of the windings 602 and 604 disposed on a thin film 606. In at least some embodiments, the windings 602 and 604 are disposed on both sides of the thin film 606. In at least some embodiments, the winding 602 is disposed on a first side of the thin film 606 and the winding 604 is disposed on a second side of the thin film 606. In preferred embodiments, the windings 602 and 604 are disposed on the thin film 606 such that when the thin film 606 is disposed around the magnet 426 (or the housing 432), the windings 602 and 604 are offset from one another by 90 degrees.

Figure 7:
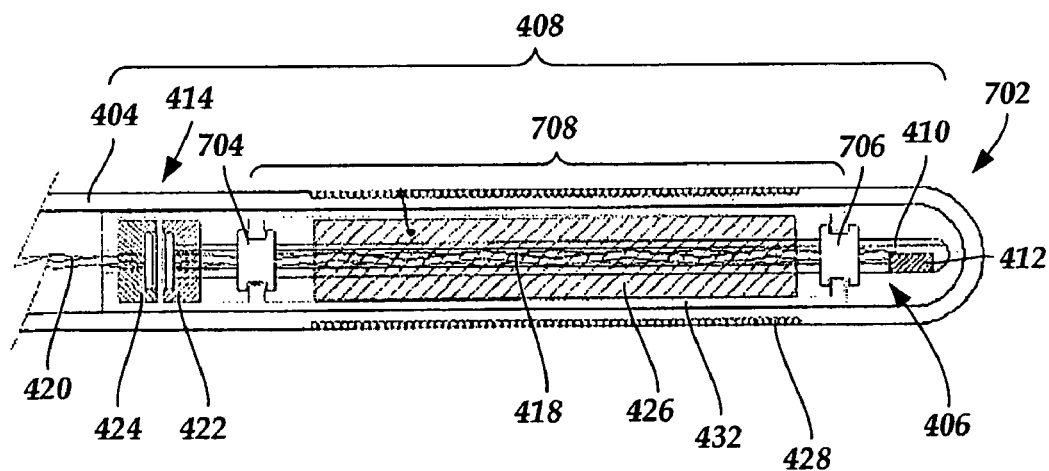
FIG. 7 is a schematic longitudinal cross-sectional view of another embodiment of a distal end of a catheter, the distal end of the catheter including an imaging core with a motor and drag-reducing elements disposed on either end of the motor, according to the invention.

It is undesirable to have rotating portions of the imaging core directly contacting stationary portions of the distal end of the catheter. Relative motion between rotating portions of the imaging core (e.g., the rotating driveshaft, the magnet, and the like) and the stationary components of the distal end of the catheter (e.g., the stator, the housing, and the like) may produce a frictional drag. FIG. 7 is a schematic longitudinal cross-sectional view of another embodiment of a distal end of a catheter 702. The catheter 702 includes drag reducing elements 704 and 706 disposed on each end of a motor 708. The drag reducing elements 704 and 706 may include any suitable device for reducing drag including, for example, one or more bushings, one or more bearings, or the like or combinations thereof.

Other drag reducing techniques may also be employed instead of, or in addition to, the drag reducing elements 704 and 706. For example, in at least some embodiments, the housing (432 in FIG. 4) is formed, at least in part, from a conductive material (e.g., carbon fiber and the like). In at least some embodiments, the rotation of the magnet (426 in FIG. 4) produces eddy currents which may increase as the angular velocity of the magnet increases. Once a critical angular velocity is met or exceeded, the eddy currents may cause the magnet to levitate. In a preferred embodiment, the conductive material of the housing has conductivity high enough to levitate the magnet (426 in FIG. 4) to a position equidistant from opposing sides of the housing, yet low enough to not shield the magnet (426 in FIG. 4) from the magnetic field produced by the windings (602 and 604 of FIG. 6).

As another example of a drag reducing technique, a space between the magnet 426 and the housing 432 may be filled with a ferrofluid (e.g., a suspension of magnetic nano-particles, such as available from the Ferrotec Corp., Santa Clara, Calif.). The ferrofluid is attracted to the magnet 426 and remains positioned at an outer surface of the magnet 426 as the magnet 426 rotates. The fluid shears near the walls of non-rotating surfaces, such that the rotating magnet 426 does not physically contact these non-rotating surfaces. The resulting viscous drag torque on the magnet 426 increases in proportion to the rotation frequency of the magnet 426, and may be reduced relative to a non-lubricated design.

In at least some embodiments, the one or more transducers are stationary within the imaging core and direct an acoustic signal onto a rotating mirror. Employing a fixed transducer and a rotating mirror may eliminate the need for a transformer. Transformers have several disadvantages including, for example, a loss in energy amplitude through inductance between components, phase-shifting IVUS waveforms, financial expense, and manufacturing difficulty. Additionally, eliminating the transformer may have several advantages. For example, the imaging core may be shorter in length than an imaging core with a transformer. As discussed above, the portion of the catheter in which the imaging core is disposed is typically stiffer than other portions of the catheter. Thus, reducing the length of the imaging core may allow the catheter to navigate through sharper turns in patient vasculature.

Figure 8:
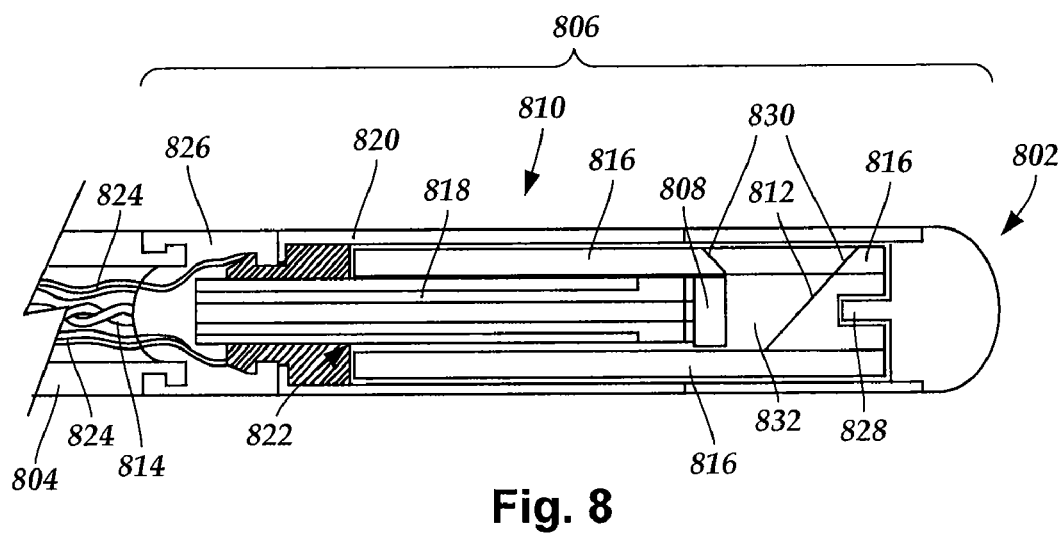
FIG. 8 is a schematic longitudinal cross-sectional view of yet another embodiment of a distal end of a catheter, the distal end of the catheter including an imaging core with a motor, one or more stationary transducers, and a rotating mirror, according to the invention.

In at least some embodiments, the rotatable mirror is positioned distal to the one or more fixed transducers. FIG. 8 is a schematic longitudinal cross-sectional view of yet another embodiment of a distal end of a catheter 802. The catheter 802 defines a lumen 804 within which an imaging core 806 is disposed. The imaging core 806 includes one or more fixed transducers 808, a motor 810, and a rotating mirror 812 distal to the one or more transducers 808. The one or more transducers 808 are electrically coupled to the control module (104 in FIG. 1) via one or more transducer conductors 814.

The motor 810 includes a rotating magnet 816 and two inner windings 818, or two outer windings 820, or one inner winding 818 and one outer winding 820. The magnet 816 may be formed from many different magnetic materials suitable for implantation including, for example, neodymium-iron-boron, or the like. In at least some embodiments, the magnet 816 is cylindrical. In at least some embodiments, the magnet 816 defines an aperture 822. In at least some embodiments, the magnet 816 has a magnetization vector that is perpendicular to the longitudinal axis of the magnet 816.

In at least some embodiments, the windings 818 or 820 include two perpendicularly-oriented windings (see e.g., 502 and 504 in FIG. 5) which provide a rotating magnetic field to torque the magnet 816. The windings 818 or 820 are provided with power from the control module (104 in FIG. 1) via one or more motor conductors 824. In at least some embodiments, a support hub 826 is positioned at a proximal end of the imaging core 806. In at least some embodiments, at least one of the windings 818 and 820 or the one or more transducers 808 are cantilevered from the support hub 826.

In at least some embodiments, the rotating mirror 812 is disposed in the aperture 822, with the one or more fixed transducers 808 disposed either proximal to the magnet 816 or in the aperture 822. In at least some embodiments, the rotating mirror 812 is disposed distally from the magnet 816, with the one or more fixed transducers 808 disposed either proximal to the magnet 816, inside the aperture 822 of the magnet 816, or distal to the magnet 816. In at least some embodiments, the rotating mirror 812 is coupled to an inner surface of the magnet 816. In at least some embodiments, the rotating mirror 812 is fixedly coupled to the magnet 816 such that the mirror 812 rotates with the magnet 816. In at least some embodiments, the mirror 812 is held in position by one or more supports 828 positioned distally from the mirror 812. In at least some embodiments, the mirror 812 is held in position such that a reflective surface of the mirror 812 is not obstructed by either the magnet 816 or the one or more supports 828 as the mirror 812 rotates during operation.

In at least some embodiments, acoustic signals may be emitted from the one or more fixed transducers 808 towards the rotating mirror 812 and be redirected to an angle that is not parallel to the longitudinal axis of the magnet 816. In at least some embodiments, acoustic signals are redirected to a plurality of angles that are within a 120 degree range with respect to the transverse axis of the magnet 816. In at least some embodiments, acoustic signals are redirected to a plurality of angles that are within a 90 degree range with respect to the transverse axis of the magnet 816. In at least some embodiments, acoustic signals are redirected to a plurality of angles that are within a 120 degree range with respect to the transverse axis of the magnet 816 such that the plurality of angles are centered on an angle that is perpendicular to the longitudinal axis of the magnet 816. In at least some embodiments, acoustic signals are redirected to a single angle that is perpendicular to the longitudinal axis of the magnet 816. In at least some embodiments, acoustic signals are redirected to a single angle that is not perpendicular to the longitudinal axis of the magnet 816. In at least some embodiments, a notch (or window, fenestration, or the like) with side walls 830 is formed in the magnet 816 to provide an acoustic opening through which acoustic signals may be transmitted from the catheter 802. In at least some embodiments, an acoustically transparent membrane may be disposed across the notch so that a region 832 between the one or more transducers 808 and the mirror 812 is fluidtight.

In at least some embodiments, the region 832 between the one or more transducers 808 and the mirror 812 is filled with an airless fluid with impedance that matches tissue or fluid surrounding the distal end of the catheter 802. In at least some embodiments, the region 832 between the one or more transducers 808 and the mirror 812 is filled with a ferrofluid. In at least some embodiments, in addition to the region 832, one or more spaces may be formed along at least a portion of the surface area of the magnet 816 when the magnet 816 is disposed in the catheter 802. In at least some embodiments, the one or more spaces surrounding at least a portion of the surface area of the magnet 816 are filled with ferrofluid. It may be an advantage to surround the magnet with ferrofluid because the ferrofluid is attracted to the magnet 816. If enough of the surface area of the magnet 816 is accessible by the ferrofluid, the ferrofluid may cause the magnet 816 to float, thereby potentially reducing friction between the magnet 816 and other contacting surfaces which may not rotate with the magnet 816 during operation.

In at least some embodiments, the mirror 812 includes a reflective surface that is non-planar. In at least some embodiments, the reflective surface of the mirror 812 is concave. It may be an advantage to employ a concaved reflective surface to improve focusing, thereby improving lateral resolution of acoustic pulses emitted from the catheter 802. In at least some embodiments, the reflective surface of the mirror 812 is convex. In at least some embodiments, the shape of the reflective surface of the mirror 812 is adjustable. It may be an advantage to have an adjustable reflective surface to adjust the focus or depth of field for imaging tissues at variable distances from the mirror 812. In at least some embodiments, the mirror 812 is a coated membrane stretched over a space that contains air or other compressible substance. When the fluid pressure of the region 832 between the one or more transducers 808 and the mirror 812 increases, the reflective surface of the mirror 812 may deflect to produce a concave surface.

Figure 9:
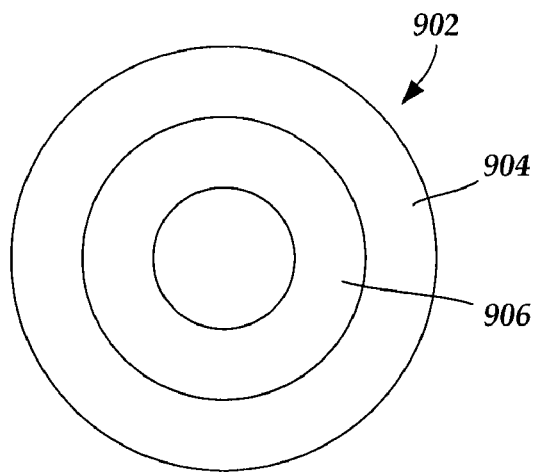
FIG. 9 is a schematic transverse cross-sectional view of one embodiment of a transducer, according to the invention.

In at least some embodiments, the one or more transducers include a plurality of annuli. In at least some embodiments, at least one of the annuli resonates at a frequency that is different from at least one of the remaining annuli. FIG. 9 is a schematic transverse cross-sectional view of one embodiment of a transducer 902 with a plurality of annuli, such as annulus 904 and annulus 906. In at least some embodiments, the annulus 904 resonates at a different frequency than the annulus 906.

Figure 10:
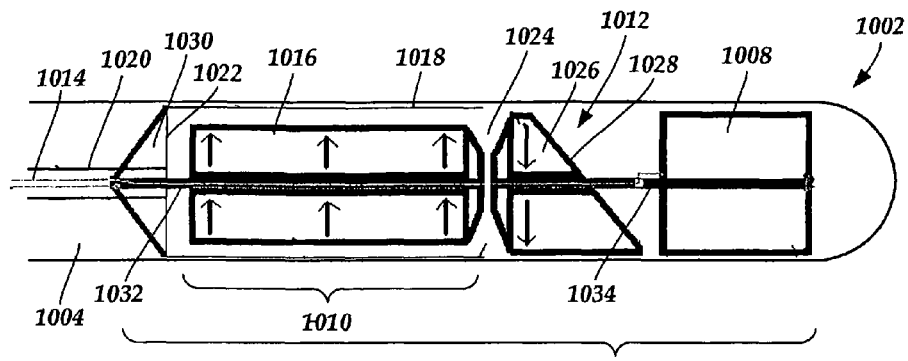
FIG. 10 is a schematic longitudinal cross-sectional view of another embodiment of a distal end of a catheter, the distal end of the catheter including an imaging core with a motor, one or more stationary transducers, and a rotating mirror, according to the invention.

In at least some embodiments, the rotatable mirror is positioned proximal to the one or more fixed transducers. FIG. 10 is a schematic longitudinal cross-sectional view of another embodiment of a distal end of a catheter 1002. The catheter 1002 defines a lumen 1004 within which an imaging core 1006 is disposed. The imaging core 1006 includes one or more fixed transducers 1008, a motor 1010, and a rotating mirror 1012 proximal to the one or more transducers 1008. The one or more transducers 1008 are electrically coupled to the control module (104 in FIG. 1) via one or more transducer conductors 1014.

The motor 1010 includes a rotating motor magnet 1016 and windings 1018. In at least some embodiments, the motor magnet 1016 is cylindrical. In at least some embodiments, the motor magnet 1016 is formed from neodymium-iron-boron. The windings 1018 are provided with power from the control module (104 in FIG. 1) via one or more motor conductors 1020. The motor 1010 is disposed in a housing 1022 with a distal end cap 1024. In at least some embodiments, space around the motor 1010 is evacuated to reduce friction. In at least some embodiments, space around the motor 1010 is filled with one or more gases to reduce friction. Many different gases may be used including, for example, nitrogen, carbon dioxide, oxygen, or the like or combinations thereof. In at least some embodiments, space around the motor 1010 includes one or more gases and is partially evacuated.

The mirror 1012 includes a magnet 1026 and a tilted reflective surface 1028. In at least some embodiments, the mirror 1012 is configured and arranged to rotate with the motor magnet 1016. In at least some embodiments, the mirror 1012 is not coupled to the end cap 1024. In at least some embodiments, the mirror magnet 1026 has an opposing magnetization direction from the motor magnet 1016, as shown in FIG. 10 by the directions of arrows on the motor magnet 1016 and the mirror magnet 1026. The motor magnet 1016 is magnetically coupled to the mirror 1012 through the end cap 1024.

The end cap 1024 can be formed from a rigid or semi-rigid material (e.g., one or more metals, alloys, plastics, composites, or the like). In at least some embodiments, the end cap 1024 is coated with a slick material (e.g., polytetrafluoroethylene, or the like) to reduce friction between the end cap 1024 and the rotating motor magnet 1016 and mirror 1012. In at least some embodiments, at least one of the motor magnet 1016 or the mirror 1012 has a tapered end contacting the end cap 1024 to reduce friction during rotation.

In at least some embodiments, the imaging core 1006 includes a support hub 1030 disposed at a distal end of the imaging core 1006. In at least some embodiments, the windings 1018 are supported on one end by the support hub 1030 and on the opposite end by the end cap 1024. In at least some embodiments, the motor 1010 includes a motor shaft 1032 providing a longitudinal axis about which the motor magnet 1016 rotates. In at least some embodiments, the motor shaft 1032 is coupled on one end by the support hub 1030 and on the opposite end by the end cap 1024. In at least some embodiments, the one or more transducers 1008 are coupled to a transducer shaft 1034 extending distally from the end cap 1024. In at least some embodiments, the mirror 1012 defines an aperture through which the transducer shaft 1034 extends. In at least some embodiments, the one or more transducer conductors 1014 are at least partially disposed in the transducer shaft 1034. In at least some embodiments, the one or more transducer conductors 1014 are at least partially disposed in the motor shaft 1032. In alternate embodiments, the one or more transducer conductors 1014 extend around an outer surface of one or more of the motor 1010 or the mirror 1012.

In at least some embodiments, acoustic signals may be emitted from the one or more transducers 1008 towards the mirror 1012 and be redirected to an angle that is not parallel to the longitudinal axis of the motor magnet 1016. In at least some embodiments, acoustic signals are redirected to a plurality of angles that are within a 120 degree range with respect to the transverse axis of the motor magnet 1016. In at least some embodiments, acoustic signals are redirected to a plurality of angles that are within a 90 degree range with respect to the transverse axis of the motor magnet 1016. In at least some embodiments, acoustic signals are redirected to a plurality of angles that are within a 120 degree range with respect to the transverse axis of the motor magnet 1016 such that the plurality of angles are centered on an angle that is perpendicular to the longitudinal axis of the motor magnet 1016. In at least some embodiments, acoustic signals are redirected to a single angle that is perpendicular to the longitudinal axis of the motor magnet 1016. In at least some embodiments, acoustic signals are redirected to a single angle that is not perpendicular to the transverse axis of the motor magnet 1016.

Figure 11:
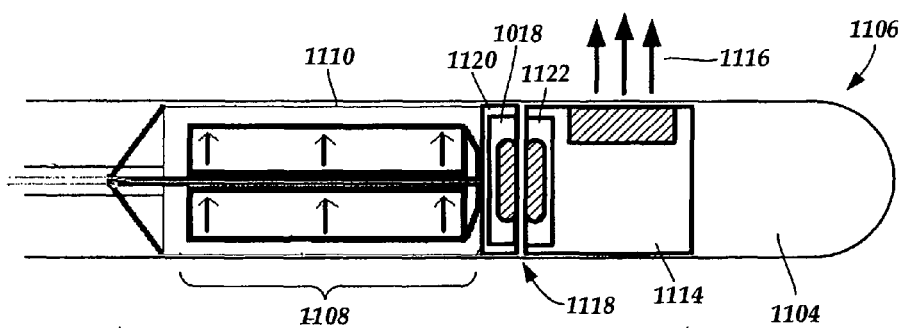
FIG. 11 is a schematic longitudinal cross-sectional view of yet another embodiment of a distal end of a catheter, the distal end of the catheter including an imaging core with a motor, one or more rotating transducers, and a transformer, according to the invention.

In alternate embodiments, the imaging core described above can be implemented using one or more rotating transducers and a transformer without using a mirror. FIG. 11 shows a longitudinal cross-sectional view of one embodiment of an imaging core 1102 disposed in a distal end of a lumen 1104 of a catheter 1106. The imaging core 1102 includes a motor 1108 disposed in a housing 1110 with an end cap 1112 that may be rigid or semi-rigid. The imaging core 1102 also includes one or more transducers 1114 disposed distal to the motor 1108. In at least some embodiments, a magnet is attached to the one or more transducers 1114. The one or more transducers 1114 (via the attached magnet) are magnetically coupled to the motor 1108 through the end cap 1112. In at least some embodiments, the one or more transducers 1114 are positioned such that the acoustic signals output from the one or more transducers 1114 are directed at angles that are not parallel with to the longitudinal axis of the motor 1108, as shown by arrows 1116. In at least some embodiments, a transformer 1118 with a stationary component 1120 and a rotating component 1122 is used to power the one or more transducers 1114. In at least some embodiments, the stationary component 1120 is disposed within the end cap 1112 and the rotating component 1122 is disposed within the one or more transducers 1114.

In at least some embodiments, the windings include a single turn of wire. As shown above, the torque on the motor (e.g., 810 in FIG. 8) is given by:

$$\tau = 2MV(NI)/(\pi D\sqrt{(1+(D/L)^2)});$$

wherein the only dependence of torque on the windings is through the product NI. For example, the same result is obtained regardless of whether 0.77 amps flow through windings with 8 turns, or 6.2 amps flow through windings with 1 turn. Heat generation will be the same as long as the total cross-sectional area of the windings is the same. For example, one line two mills high and sixteen mills wide heats equivalent to eight lines two mills high and two mills wide. Accordingly, in at least some embodiments, each winding includes a single turn.

Figure 12:
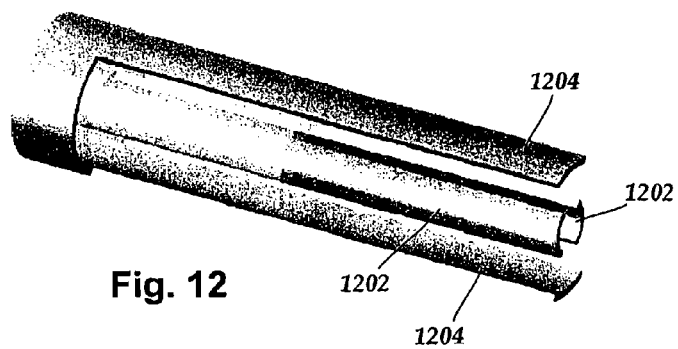
FIG. 12 is a schematic perspective view of one embodiment of a two-phase winding geometry configured and arranged for forming a rotating magnetic field around a motor, according to the invention.

FIG. 12 is a schematic perspective view of one embodiment of a portion of a first single-turn winding 1202 and a second single-turn winding 1204 configured and arranged for disposing around the magnet (816 in FIG. 8). In at least some embodiments, the first single-turn winding 1202 and the second single-turn winding 1204 are configured and arranged for disposing on separate surfaces of the magnet (816 in FIG. 8). For example, in at least some embodiments, the first single-turn winding 1202 is configured and arranged to be disposed along an inner surface of the magnet (816 in FIG. 8) and the second single-turn winding 1204 is configured and arranged to be disposed along an outer surface of the magnet (816 in FIG. 8). The single-turn windings 1204 and 1206 may be formed from any type of conductive material suitable for implantation into a patient. It may be an advantage to employ single-turn windings, and disposing the first single-turn winding 1202 and the second single-turn winding 1204 along separate surfaces in order to eliminate crossovers from the top and bottom side of the winding circuit.

Figure 13:
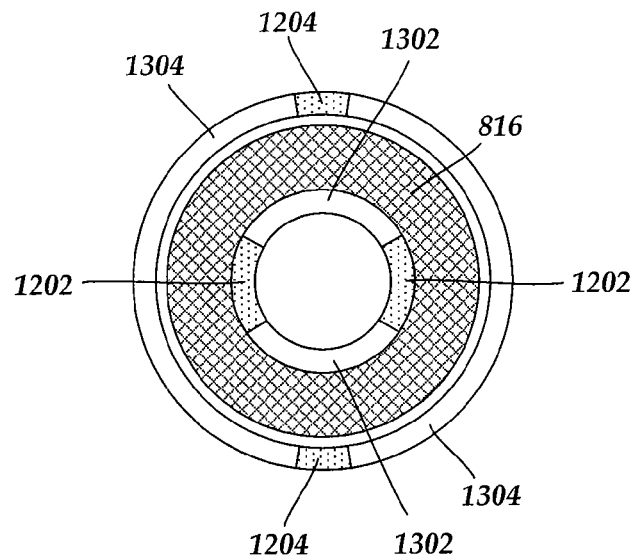
FIG. 13 is a schematic transverse cross-sectional view of one embodiment of the two single-turn windings of FIG. 12 disposed around a motor, according to the invention.

FIG. 13 is a schematic transverse cross-sectional view of one embodiment of the first and second single-turn windings 1202 and 1204, respectively, disposed around the magnet (816 in FIG. 8). The single-turn windings 1202 and 1204 may be disposed directly along the magnet 816. In at least some embodiments, the single-turn windings 1202 and 1204 may be imbedded in non-conductive tubing in order to maintain a relative thickness of the catheter (802 in FIG. 8) along a transverse axis of the catheter (802 in FIG. 8). For example, the first single-turn winding 1202 is shown in FIG. 13 as being imbedded in a non-conductive tube 1302 which is disposed along an inner side of the magnet 816. Similarly, the second single-turn winding 1204 is shown in FIG. 13 as being imbedded in a non-conductive tubing 1304 disposed along an outer side of the magnet 816.

The second single-turn winding 1204 may exert more torque than the first single-turn winding 1202 because the second single-turn winding 1204 has a larger diameter than the second single-turn winding 1204. Thus, the second single-turn winding 1204 may not need to input as much current as the first single-turn winding 1202 during operation. Accordingly, in at least some embodiments, the second single-turn winding 1204 is not as thick as the first single-turn winding 1202.

In at least some embodiments, up to six amps of current may be utilized by the motor. Thus, in a preferred embodiment, the components of the catheter and imaging core are capable of withstanding up to six amps of current without heating. Low power electronic components are currently available to source six amps of current at low voltage. Additionally, previous studies have shown that flexible stranded leads with an equivalent diameter of approximately 0.015 inches (0.04 cm) can withstand up to six amps of current, while also being capable to fitting through a one-millimeter diameter catheter.

It will be understood that there are many different multiple-phase winding geometries and current configurations that may be employed to form a rotating magnetic field. For example, a motor may include, for example, a two-phase winding, a three-phase winding, a four-phase winding, a five-phase winding, or more multiple-phase winding geometries. It will be understood that a motor may include many other multiple-phase winding geometries. In a two-phase winding geometry, as discussed above, the currents in the two windings are out of phase by 90°. For a three-phase winding, there are three lines of sinusoidal current that are out of phase by zero, 120°, and 240°, with the three current lines also spaced by 120°, resulting in a uniformly rotating magnetic field that can drive a cylindrical motor magnet magnetized perpendicular to the current lines.

Figure 14:
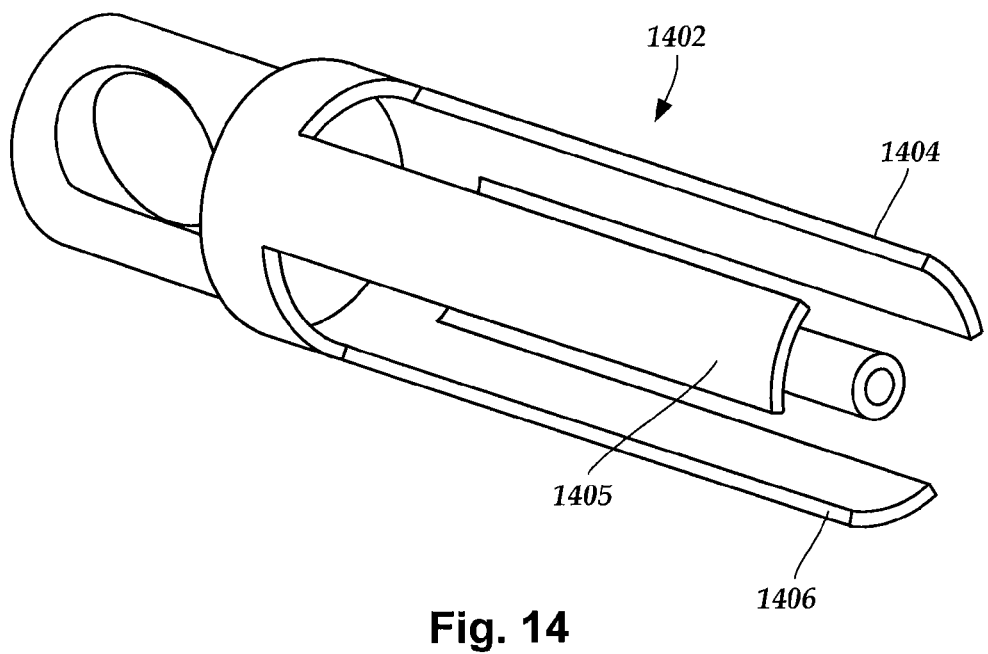
FIG. 14 is a schematic perspective view of one embodiment of a three-phase winding geometry configured and arranged for forming a rotating magnetic field around a motor, according to the invention.

FIG. 14 is a schematic perspective view of one embodiment of a three-phase winding geometry 1402 configured and arranged for forming a rotating magnetic field around a magnet (see e.g., 816 in FIG. 8). The three-phase winding 1402 includes three windings, or lines, 1404-1406. In at least some embodiments, multiple windings may utilize a single cylindrical surface of the magnet (816 of FIG. 8) with no crossovers. Such a winding may occupy a minimal volume in an imaging core. Although other geometries may also form a rotating magnetic field, the three-phase geometry 1402 may have the advantages of allowing for a more compact motor construction than other geometries.

An exceptional property of a three-phase winding geometry 1402 is that only two of the three lines 1404-1406 needs to be driven, while the third line is a common return that mathematically is equal to the third phase of current. This can be verified by noting that:

$$\text{Sin}(\omega t) + \text{Sin}(\omega t + 120°) = -\text{Sin}(\omega t + 240°)$$

For a three-phase winding geometry 1402, current is driven into two lines with the zero and 120° phase shift of the two terms on the left side of this identity. The sum of the two terms returns on the common line with exactly the correct 240° phase shift on the right side of this equation needed to create the rotating magnetic field. It will be understood that the minus sign indicates that the return current is in the opposite direction of driven current.

In at least some embodiments, the three unsupported lines 1404-1406 may be supported by a substrate to increase mechanical stability. In at least some embodiments, the lines 1404-1406 are constructed from a solid metal tube, leaving most of the metal in tact, and removing only metal needed to prevent shorting of the lines 1404-1406. In at least some embodiments, the removed portions are backfilled with a non-conductive material.

The above specification, examples and data provide a description of the manufacture and use of the composition of the invention. Since many embodiments of the invention can be made without departing from the spirit and scope of the invention, the invention also resides in the claims hereinafter appended.

What is claimed as new and desired to be protected by Letters Patent of the United States is:

1. A catheter assembly for an intravascular ultrasound system, the catheter assembly comprising:
    a catheter having a longitudinal length, a distal end, and a proximal end, the catheter comprising a lumen extending along the longitudinal length of the catheter from the proximal end to the distal end;
    an imaging core with a longitudinal length that is substantially less than the longitudinal length of the catheter, the imaging core configured and arranged for inserting into the lumen to the distal end of the catheter, the imaging core comprising
        a rotatable driveshaft having a distal end and a proximal end,
        at least one rotatable transducer disposed at and coupled to the distal end of the driveshaft, the at least one transducer configured and arranged for transforming applied electrical signals to acoustic signals and also for transforming received echo signals to electrical signals,
        a transformer disposed at the proximal end of the driveshaft,
        at least one imaging core conductor coupling the at least one transducer to the transformer, and
        a motor coupled to the driveshaft between the one or more transducers and the transformer, the motor comprising a rotatable magnet and at least two magnetic field windings disposed around at least a portion of the magnet, the magnet having a longitudinal axis and an aperture defined along the longitudinal axis of the magnet;

at least one catheter conductor electrically coupled to the transformer and extending to the proximal end of the catheter; and at least one motor conductor electrically coupled to the magnetic field windings and extending to the proximal end of the catheter, wherein the assembly does not include a mirror.

2. The catheter assembly of claim 1, wherein the imaging core further comprises a sensing device, the sensing device configured and arranged for sensing an angular position of the magnet.

3. The catheter assembly of claim 2, wherein the sensing device is configured and arranged to control an amount of current applied to the magnetic field windings using the received angular position of the magnet.

4. The catheter assembly of claim 1, wherein the catheter has a transverse diameter that is not greater than one millimeter.

5. The catheter assembly of claim 1, wherein at least one of the at least one imaging core conductor or the driveshaft extends through the aperture of the magnet.

6. The catheter assembly of claim 1, wherein the transformer comprises a rotating component and a stationary component spaced apart from one another, wherein the rotating component is electrically coupled to the at least one imaging core conductor and the stationary component is electrically coupled to the at least one catheter conductor.

7. The catheter assembly of claim 1, wherein the magnet is disposed in a housing.

8. The catheter assembly of claim 7, wherein the housing is formed from a conductive material with conductivity high enough to levitate the magnet when the magnet rotates at an operational angular velocity.

9. The catheter assembly of claim 7, wherein the magnetic field windings are disposed on a thin film.

10. The catheter assembly of claim 9, wherein the thin film is disposed on the housing.

11. An intravascular ultrasound imaging system comprising:

the catheter assembly of claim 1; and a control module coupled to the imaging core, the control module comprising a pulse generator configured and arranged for providing electric signals to the at least one transducer, the pulse generator electrically coupled to the at least one transducer via the one or more conductors and the transformer, and a processor configured and arranged for processing received electrical signals from the at least one transducer to form at least one image, the processor electrically coupled to the at least one transducer via the one or more conductors.

12. A catheter assembly for an intravascular ultrasound system, the catheter assembly comprising:

a catheter having a longitudinal length, a distal end, and a proximal end, the catheter comprising a lumen extending along the longitudinal length of the catheter from the proximal end to the distal end;

an imaging core with a longitudinal length that is substantially less than the longitudinal length of the catheter, the imaging core configured and arranged for inserting into the lumen to the distal end of the catheter, the imaging core comprising a motor comprising a rotatable magnet and at least two magnetic field windings disposed around at least a portion of the magnet, the magnet having a longitudinal axis and an aperture defined along the longitudinal axis of the magnet, at least one transducer disposed in the imaging core, wherein the at least one transducer is configured and arranged for transforming applied electrical signals to acoustic signals and also for transforming received echo signals to electrical signals, and wherein the at least one transducer is fixed in position such that the at least one transducer does not rotate with the magnet, and a mirror positioned distal to the at least one transducer, wherein the mirror is tilted at an angle such that when an acoustic beam is emitted from the at least one transducer to the mirror, the acoustic beam is redirected in a direction that is not parallel the longitudinal axis of the magnet, and wherein the rotation of the magnet causes the mirror to rotate;

at least one catheter conductor electrically coupled to the one or more transducers and extending to the proximal end of the catheter; and at least one motor conductor electrically coupled to the magnetic field windings and extending to the proximal end of the catheter, wherein the at least one transducer is disposed in the aperture defined in the magnet.

13. The catheter assembly of claim 12, wherein the magnetic field windings each comprise a single turn of a conductive material.

14. The catheter assembly of claim 12, the mirror comprises a non-planar reflective surface.

15. The catheter assembly of claim 12, wherein the at least one transducer comprises a plurality of annuli, at least one annulus configured and arranged to resonate at a frequency that is different from at least one other annulus.

16. The catheter assembly of claim 12, wherein the mirror is disposed in the aperture defined in the magnet.

17. The catheter assembly of claim 12, wherein the magnet defines a notch through which an acoustic signal, emitted from the at least one transducer and redirected from the mirror, transmits through.

18. The catheter assembly of claim 12, wherein the at least one transducer and the mirror are disposed in a fluid-filled region.

19. The catheter assembly of claim 18, wherein the magnet is at least partially surrounded by a ferrofluid.

20. A catheter assembly for an intravascular ultrasound system, the catheter assembly comprising:

a catheter having a longitudinal length, a distal end, and a proximal end, the catheter comprising a lumen extending along the longitudinal length of the catheter from the proximal end to the distal end;

an imaging core with a longitudinal length that is substantially less than the longitudinal length of the catheter, the imaging core configured and arranged for inserting into the lumen to the distal end of the catheter, the imaging core comprising a motor disposed in a housing with a distal end cap, the motor comprising a rotatable motor magnet and at least two magnetic field windings disposed around at least a portion of the motor magnet, the magnet having a longitudinal axis and a motor shaft disposed along the longitudinal axis of the motor magnet, at least one transducer disposed in the imaging core, wherein the at least one transducer is configured and arranged for transforming applied electrical signals to acoustic signals and also for transforming received echo signals to electrical signals, and wherein the at least one transducer is fixed in position such that the at least one transducer does not rotate with the motor magnet, and a redirecting mirror comprising a mirror magnet having a reflective surface, the mirror positioned proximal to the at least one transducer, wherein the reflective surface is tilted at an angle such that when an acoustic beam is emitted from the at least one transducer to the reflective surface, the acoustic beam is redirected in a direction that is not parallel the longitudinal axis of the motor magnet, and wherein the mirror magnet and the motor magnet are magnetically coupled together within the end cap such that the rotation of the motor magnet causes the mirror to rotate;

at least one transducer conductor electrically coupled to the one or more transducers and extending to the proximal end of the catheter; and at least one motor conductor electrically coupled to the magnetic field windings and extending to the proximal end of the catheter.

21. The catheter assembly of claim 20, wherein the at least one transducer is coupled to the end cap via a transducer shaft.

22. The catheter assembly of claim 20, wherein the imaging core further comprises a support hub disposed at a proximal end of the imaging core.

23. The catheter assembly of claim 22, wherein the motor shaft extends from the support hub to the end cap.

24. The catheter assembly of claim 20, wherein the housing is at least partially evacuated.

25. A catheter assembly for an intravascular ultrasound system, the catheter assembly comprising:

a catheter having a longitudinal length, a distal end, and a proximal end, the catheter comprising a lumen extending along the longitudinal length of the catheter from the proximal end to the distal end;

an imaging core with a longitudinal length that is substantially less than the longitudinal length of the catheter, the imaging core configured and arranged for inserting into the lumen to the distal end of the catheter, the imaging core comprising a motor disposed in a housing with a distal end cap, the motor comprising a rotatable magnet and at least two magnetic field windings disposed around at least a portion of the magnet, the magnet having a longitudinal axis along which the magnet rotates, at least one rotatable transducer disposed in the imaging core, the at least one transducer comprising a transducer magnet, wherein the at least one transducer is configured and arranged for transforming applied electrical signals to acoustic signals and also for transforming received echo signals to electrical signals, and wherein the transducer magnet and the motor magnet are magnetically coupled together within the end cap such that the rotation of the motor magnet causes the at least one transducer to rotate with the motor magnet, and a transformer electrically coupled to the at least one transducer;

at least one transducer conductor electrically coupled to the transformer and extending to the proximal end of the catheter; and at least one motor conductor electrically coupled to the magnetic field windings and extending to the proximal end of the catheter.

26. The catheter assembly of claim 25, wherein the transformer comprises a stationary component and a rotating component spaced apart from one another, and wherein the stationary component is disposed in the end cap and the rotating component is disposed in the at least one transducer.

\* \* \* \* \*